United States Patent
Matsuda et al.

(10) Patent No.: US 10,330,670 B2
(45) Date of Patent: Jun. 25, 2019

(54) THERAPEUTIC OR PROPHYLACTIC AGENT FOR RETINOPATHY OF PREMATURITY, TESTING METHOD FOR RETINOPATHY OF PREMATURITY, AND SCREENING METHOD FOR THERAPEUTIC OR PROPHYLACTIC SUBSTANCE FOR RETINOPATHY OF PREMATURITY

(71) Applicants: TOKYO UNIVERSITY OF AGRICULTURE AND TECHNOLOGY, Tokyo (JP); JAPAN INNOVATIVE THERAPEUTICS, INC., Nagoya-shi, Aichi (JP)

(72) Inventors: Hiroshi Matsuda, Tokyo (JP); Akane Tanaka, Tokyo (JP)

(73) Assignees: NATIONAL UNIVERSITY CORPORATION TOKYO UNIVERSITY OF AGRICULTURE AND TECHNOLOGY, Tokyo (JP); JAPAN INNOVATION THERAPEUTICS, INC., Nagoya-Shi (JP)

( * ) Notice: Subject to any disclaimer, the term of this patent is extended or adjusted under 35 U.S.C. 154(b) by 0 days.

(21) Appl. No.: 14/437,925

(22) PCT Filed: Oct. 24, 2013

(86) PCT No.: PCT/JP2013/078849
§ 371 (c)(1),
(2) Date: Apr. 23, 2015

(87) PCT Pub. No.: WO2014/065374
PCT Pub. Date: May 1, 2014

(65) Prior Publication Data
US 2015/0276718 A1    Oct. 1, 2015

(30) Foreign Application Priority Data

Oct. 24, 2012   (JP) .................................. 2012-234729
Mar. 27, 2013   (JP) .................................. 2013-066295

(51) Int. Cl.
*G01N 33/573*    (2006.01)
*G01N 33/53*    (2006.01)
(Continued)

(52) U.S. Cl.
CPC ....... *G01N 33/5044* (2013.01); *A61K 9/0019* (2013.01); *A61K 9/0048* (2013.01);
(Continued)

(58) Field of Classification Search
None
See application file for complete search history.

(56) References Cited

U.S. PATENT DOCUMENTS 7,767,685 B2    8/2010   Baraldi et al.
2009/0253765 A1   10/2009   Oohashi et al.
(Continued)

FOREIGN PATENT DOCUMENTS

EP    2 455 091 A1    5/2012
JP    2006-348023 A    12/2006
(Continued)

OTHER PUBLICATIONS

Machalinska et al., Evaluation of VEGF and IGF-1 plasma levels in preterm infants—potential correlation with retinopathy of prematurity, clinical implications. Klin Oczna. 2009;111(10-12):302-6. Abstract only.*

(Continued)

*Primary Examiner* — Aurora M Fontainhas
(74) *Attorney, Agent, or Firm* — Birch, Stewart, Kolasch & Birch, LLP

(57) ABSTRACT

Provided are a therapeutic or prophylactic agent for retinopathy of prematurity (ROP) that is suited to the pathogenic (Continued)

mechanism of ROP and a method of testing for ROP. The therapeutic or prophylactic agent for ROP uses at least one substance from the group consisting of inhibitors against tryptase derived from mast cells and/or mast cell stabilizers as an active ingredient. The testing method for ROP includes detecting a marker substance that can be released by degranulation of mast cells in a biological sample originating from a patient and determining the presence or absence of ROP on the basis of the detected amount of the marker.

7 Claims, 7 Drawing Sheets

(51) Int. Cl.
| | |
|---|---|
| *C12Q 1/25* | (2006.01) |
| *G01N 33/50* | (2006.01) |
| *A61K 45/00* | (2006.01) |
| *A61K 31/352* | (2006.01) |
| *G01N 33/68* | (2006.01) |
| *A61K 45/06* | (2006.01) |
| *A61K 9/00* | (2006.01) |
| *A61K 31/245* | (2006.01) |
| *A61K 47/10* | (2017.01) |
| *C07K 16/40* | (2006.01) |

(52) U.S. Cl.
CPC .......... *A61K 31/245* (2013.01); *A61K 31/352* (2013.01); *A61K 45/00* (2013.01); *A61K 45/06* (2013.01); *A61K 47/10* (2013.01); *C07K 16/40* (2013.01); *G01N 33/5023* (2013.01); *G01N 33/5047* (2013.01); *G01N 33/573* (2013.01); *G01N 33/6893* (2013.01); *G01N 2333/96441* (2013.01); *G01N 2800/164* (2013.01)

(56) References Cited

U.S. PATENT DOCUMENTS

| | | | |
|---|---|---|---|
| 2009/0318545 | A1 | 12/2009 | Silver et al. |
| 2011/0237543 | A1 | 9/2011 | Kang et al. |
| 2011/0293631 | A1* | 12/2011 | Thumbikat .......... A61K 39/395 424/158.1 |
| 2013/0251823 | A1 | 9/2013 | Fujimori et al. |
| 2013/0310316 | A1 | 11/2013 | Hellstrom et al. |

FOREIGN PATENT DOCUMENTS

| | | |
|---|---|---|
| JP | 2010-524928 A | 7/2010 |
| JP | 2011-37830 A | 2/2011 |
| JP | 2012-505928 A | 3/2012 |
| WO | WO 03/053366 A2 | 7/2003 |
| WO | WO 2008/130315 A1 | 10/2008 |
| WO | WO 2010/047500 A2 | 4/2010 |
| WO | WO 2011/025734 A1 | 3/2011 |

OTHER PUBLICATIONS

Sood et al., Perinatal systemic inflammatory response syndrome and retinopathy of prematurity. Pediatr Res. Apr. 2010;67(4):394-400.*
Silveira et al., Assessment of the Contribution of Cytokine Plasma Levels to Detect Retinopathy of Prematurity in Very Low Birth Weight Infants. Investigative Ophthalmology & Visual Science Mar. 2011, vol. 52, 1297-1301. Mar. 10, 2011.*
Patel et al., Mast cell-derived neurotrophin 4 mediates allergen-induced airway hyperinnervation in early life. Mucosal Immunology advance online publication Feb. 10, 2016, 1-11.*
Wernersson et al., Mast cell secretory granules: armed for battle. Nat Rev Immunol. Jul. 2014;14(7):478-94.*
Blair et al., Human Mast Cells Stimulate Vascular Tube Formation.J Clin Invest. Jun. 1, 1997;99(11):2691-700.*
Ribatti et al., Neovascularization and mast cells with tryptase activity increase simultaneously in human pterygium. J Cell Mol Med. May-Jun. 2007;11(3):585-9.*
Al-Shabrawey et al., Targeting Neovascularization in Ischemic Retinopathy: Recent Advances. Expert Rev Ophthalmol. Jun. 2013; 8(3): 267-286.*
Alvarez et al., "Selective inhibition of retinal angiogenesis by targeting PI3 kinase", PloS one, Nov. 2009, vol. 4, No. 11, e7867, pp. 1-10.
Aoike et al., "Effect of Tranilast on Retinal Vessels of Streptozotocin-Diabetic Rat", Journal of the Eye, 1999, vol. 16, No. 10, pp. 1413-1416.
Cantarella et al., "Nerve growth factorendothelial cell interaction leads to angiogenesis in vitro and in vivo," The FASEB Journal, express article 10.1096/fj.01-1000fje. Published online Jun. 21, 2002, vol. 16, pp. 1307-1309.
Garcia-Roman et al., "VEGF secretion during hypoxia depends on free radicals-induced Fyn kinase activity in mast cells", Biochemical and Biophysical Research Communications, 2010, vol. 401, No. 2, pp. 262-267.
Gordon et al., "Mast cells as a source of both preformed and immunologically inducible TNF-alpha/cachectin", Nature, Jul. 19, 1990, vol. 346, pp. 274-276.
Grutzkau et al., "Detection of Intracellular Interleukin-8 in Human Mast Cells: Flow Cytometry as a Guide for Immunoelectron Microscopy", The Journal of Histochemistry & Cytochemistry, 1997, vol. 45, No. 7, pp. 935-945.
International Search Report issued in PCT/JP2013/078849, dated Dec. 24, 2013.
Isaji et al., "Tranilast inhibits the proliferation, chemotaxis and tube formation of human microvascular endothelial cells in vitro and angiogenesis in vivo", British Journal of Pharmacology, 1997, vol. 122, No. 6, pp. 1061-1066.
Koyama et al., "Tranilast inhibits protein kinase C-dependent signalling pathway linked to angiogenic activities and gene expression of retinal microcapillary endothelial cells", British Journal of Pharmacology, 1999, vol. 127, No. 2, pp. 537-545.
Muramatsu et al.,"Chymase as a Proangiogenic Factor (A Possible Involvement of Chymase-Angiotensin-Dependent Pathway in the Hamster Sponge Angiogenesis Model)", The Journal of Biological Chemistry, Feb. 25, 2000, vol. 275, No. 8 pp. 5545-5552.
Okamoto et al., "Tranilast Treatment for Macular Edema in Two Patients with Central Retinal Vein Occlusion", Journal of the Eye, 1998, vol. 15, No. 9, pp. 1317-1321.
PCT/ISA/237—Issued in PCT/JP2013/078849, dated Dec. 24, 2013.
Pierce et al., "Vascular endothelial growth factor/vascular permeability factor expression in a mouse model of retinal neovascularization", Proceedings of the National Academy of Sciences of the United States of America, Jan. 1995, vol. 92, No. 3, pp. 905-909.
Sapieha et al., "Retinopathy of prematurity: understanding ischemic retinal vasculopathies at an extreme of life", The Journal of Clinical Investigation, Sep. 2010, vol. 120, No. 9, pp. 3022-3032.
Theoharides et al., "Differential release of serotonin and histamine from mast cells", Nature, Macmillan Journals Ltd., May 20, 1982, vol. 297, pp. 229-231.
Yu et al., "Effects of the phosphatidylinositol 3-kinase inhibitor in a mouse model of retinal neovascularization", Ophthalmic Research, 2008, vol. 40, No. 1, pp. 19-25.
Database Medline, "[Histopathological study of retrolental membranes secondary to persistent hyperplastic primary vitreous]," Database Accession No. NLM20654058, Apr. 2010, 2 pages, XP-002757111.
Extended European Search Report for European Application No. 13848627.9, dated May 19, 2016.
Lee, "An update on necrotizing enterocolitis: pathogenesis and preventive strategies," Korean Journal of Pediatrics, vol. 54, No. 9, Jan. 2011, pp. 368-372, XP055269057.
Raghuveer et al., "Lactoferrin in the Preterm Infants' Diet Attenuates Iron-Induced Oxidation Products," Pediatric Research, vol. 52, No. 6, Nov. 13, 2002, pp. 964-972, XP055269073.

(56) References Cited

OTHER PUBLICATIONS

Ebihara et al., "Gankai no Tameno Sentan Iryo 20. Ganka Ryoiki ni Okeru Himan Saibogaku (Mast Cytology) no Tenkai", Journal of the Eye, 2002, vol. 19, No. 8, pp. 1049-1052.

Murakami et al., "Teisanso no Kekkan Saibo Seibutsugaku 6) Teisanso to Momaku Kekkan Shinsei", Vascular Biology & Medicine, 2006, vol. 7, No. 4, pp. 359-367.

Japanese Office Action and English translation, dated Nov. 7, 2017, for Japanese Application No. 2013-221231.

Manzoni et al., "Bovine lactoferrin supplementation for prevention of late-onset sepsis in very low-birth-weight neonates: a randomized trial," JAMA, vol. 302, No. 13, Oct. 7, 2009, pp. 1421-1428.

Pammi et al., "Oral lactoferrin for the prevention of sepsis and necrotizing enterocolitis in preterm infants," Cochrane Database of Systematic Reviews, Issue 10, Art. No. CD007137, 2011, pp. 1-29 (31 pages total).

Japanese Office Action issued in Japanese Patent Application No. 2013-221231 dated Aug. 1, 2017, with English translation.

Saito et al., "Serum Levels of Insulin-Like Growth Factor-1 and Vascular Endothelial Growth Factor in an Infant with Retinopathy of Prematurity Needing Vitreous Surgery", J. Clin. Ophthalmol., vol. 65, No. 8 (2011) pp. 1279-1283.

\* cited by examiner

THERAPEUTIC OR PROPHYLACTIC AGENT FOR RETINOPATHY OF PREMATURITY, TESTING METHOD FOR RETINOPATHY OF PREMATURITY, AND SCREENING METHOD FOR THERAPEUTIC OR PROPHYLACTIC SUBSTANCE FOR RETINOPATHY OF PREMATURITY

TECHNICAL FIELD

The present invention relates to a therapeutic or prophylactic agent for retinopathy of prematurity, a testing method for retinopathy of prematurity, and a method for screening a therapeutic or prophylactic substance for retinopathy of prematurity.

BACKGROUND ART

With the progress of intensive care for newborns made in recent years, the survival rate of infants with very low birth weight of 1,000 g or less has increased, while at the same time, due to exposure to high concentration oxygen applied during intensive cares, the incidence of retinopathy of prematurity (hereinafter may be simply referred to as "ROP") has also increased. ROP is a major blinding disease occurring in premature infants who have been exposed to high concentration oxygen. The number of patients of such disease is as large as 30,000 per year within Japan only and is constantly increasing.

Neovascularization in the retina, which is a primary pathological change caused due to ROP, is related with local ischemia and subsequent development of abnormal neovascularization. It has been known that ROP involves serious deuteropathy such as blindness that may occur due to detachment of the retina. However, a factor that regulates the occurrence of ROP has not been clarified yet. No prophylactic treatments such as control of organs to be subjected to the load from oxygenation, use of antioxidants, in particular, use of vitamin E, has been successful so far.

With respect to the therapeutic method, it has been shown that coagulation of avascular retina with laser beam and a freezing treatment of avascular retina are partially effective for prophylaxis of blindness occurring in patients of ROP (e.g., Non-Patent Document 1).

Agents effective for therapy or prophylaxis of ROP have been proposed in consideration of neovascularization. Examples of such agents include: a composition including a combination of a specific sialyloligosaccharide (e.g., Patent Document 1), an insulin-like growth factor I (IGF-1) or an analog thereof, and an insulin-like growth factor-binding protein or an analog thereof (e.g., Patent Document 2); nitrate; nitrite (e.g., Patent Document 3) and the like.

On the other hand, a mastocyte (hereinafter may also be referred to as a "mast cell") has a large number of granules inside the cell, and inside each granule, various substances known as chemotransmitters (chemical mediators) are included, such as histamine, serotonin, leukotriene, and heparin. When the mast cell is stimulated and thus activated (degranulated), these substances are released out of the cell. In this action, neovascularization is induced due to stimulation of proliferation of vascular endothelial cells applied by histamine and heparin stored in the mast cells.

In addition, it has been known that proteases such as tryptase or chymase released from a mast cell and cytokine such as tumor necrosis factor-α (TNF-α), interleukin-8, and a nerve growth factor are involved in normal neovascularization or neovascularization related to tumors (see Non-Patent Documents 2 to 5, for example).

PRIOR ART DOCUMENTS

Patent Documents

Patent Document 1: Japanese translation of PCT International Application Publication No. JP 2012-505928
Patent Document 2: Japanese translation of PCT International Application Publication No. JP 2010-524928
Patent Document 3: Japanese translation of PCT International Application Publication No. JP 2011-37830

Non-Patent Document

Non-Patent Document 1: J Clin Invest., 120, 3022-3032 (2010)
Non-Patent Document 2: J Biol Chem., 275, 5545-5552 (2000)
Non-Patent Document 3: Nature, 297, 229-231 (1982)
Non-Patent Document 4: Nature, 346, 274-276 (1990)
Non-Patent Document 5: J Histochem Cytochem., 45, 935-945 (1997)
Non-Patent Document 6: FASEB J., 16, 1307-1309 (2002)

SUMMARY OF INVENTION

Technical Problem

However, the therapeutic method using laser can decrease the incidence of blindness by only 25%, and thus vision of the patients is often low after treatment. In addition, with respect to the therapy or prophylaxis by the above-described agents, no sufficient effects of the therapy or the prophylaxis can be expected because they are not based on the pathogenic mechanism of ROP. It has not been known that mast cells are involved in the pathogenic mechanism of ROP.

Therefore, prophylactic and therapeutic strategies based on more specific targeting suited to the pathogenic mechanism of ROP has been demanded.

Accordingly, the purpose of the present invention to provide a therapeutic or prophylactic agent for ROP conforming to the pathogenic mechanism of ROP, a testing method for ROP, and a screening method for a therapeutic or prophylactic substance for ROP.

Solution to Problem

The inventors of the present invention have obtained new knowledge such that when the environment is shifted from a high oxygen concentration environment to a normal oxygen environment, severe ROP has occurred in mast cell non-knockout mice while in mast cell knockout mice, ROP has not occurred and less retinal neovascularization has occurred. The present invention has been achieved on the basis of the above-described knowledge.

The present invention is as follows.

[1] A therapeutic or prophylactic agent for retinopathy of prematurity comprising at least one compound selected from the group consisting of: inhibitors against tryptase derived from mast cells; and mast cell stabilizers as active ingredients.

[2] A method for therapy or prophylaxis for retinopathy of prematurity comprising administering the therapeutic or prophylactic agent according to the component [1] to a patient who needs therapy or prophylaxis of retinopathy of prematurity by an amount effective for the therapy or the prophylaxis.

[3] A testing method for retinopathy of prematurity including detecting marker substances that can be released by degranulation of mast cells from biological samples derived from a subject, and determining whether the subject has been affected by retinopathy of prematurity or whether the subject needs therapy or prophylaxis of retinopathy of prematurity based on a detected amount of the marker substances.

[4] A method for therapy or prophylaxis of retinopathy of prematurity including detecting marker substances that can be released by degranulation of mast cells from biological samples derived from a subject, determining whether the subject is a patient needing therapy or prophylaxis of retinopathy of prematurity on the basis of a detected amount of the marker substances, and administering a therapeutic or prophylactic agent for retinopathy of prematurity comprising at least one compound selected from the group consisting of inhibitors against tryptase derived from mast cells and mast cell stabilizers as an active ingredient to a patient needing therapy or prophylaxis of retinopathy of prematurity by an amount effective for the therapy or prophylaxis therefor.

[5] A method for screening a therapeutic or prophylactic substance for retinopathy of prematurity including subjecting mast cells to a process of inducing release of marker substances that can be released by degranulation of the mast cells, bringing the mast cells having been subjected to the marker substance release induction process into contact with a candidate substance, detecting the marker substance released from the mast cells after the contact, and screening, after determining whether the candidate substance has an activity of inhibiting release of the marker substances on the basis of a detected amount of the marker substances, the candidate substance having been determined to have a marker substance release inhibiting activity as a target substance capable of exhibiting a therapeutic or prophylactic effect for retinopathy of prematurity.

The present invention is epoch-making in the following points.
(1) Very many researches have emphasized intermediation of ocular allergy as a function of mast cells, however, no precedents other than the present invention have ever clarified that mast cells are involved in ocular diseases caused due to ischemic retinopathy.
(2) The inventors of the present invention have found that the drastic change of the oxygen concentration from a high oxygen concentration environment to a normal oxygen environment triggers the neovascularization effect of mast cells, and no precedents have ever reported such a functional change.
(3) The inventors of the present invention have found that mast cell tryptase is a primary promoter of retinal neovascularization in ROP, and no precedents have ever reported such knowledge.

Advantageous Effects of Invention

According to the present invention, a therapeutic or prophylactic agent for ROP, a testing method for ROP, and a method for screening therapeutic or prophylactic substances for ROP that are suited to the pathogenic mechanism of ROP and highly effective can be provided.

DESCRIPTION OF EMBODIMENTS

Figure 1A:
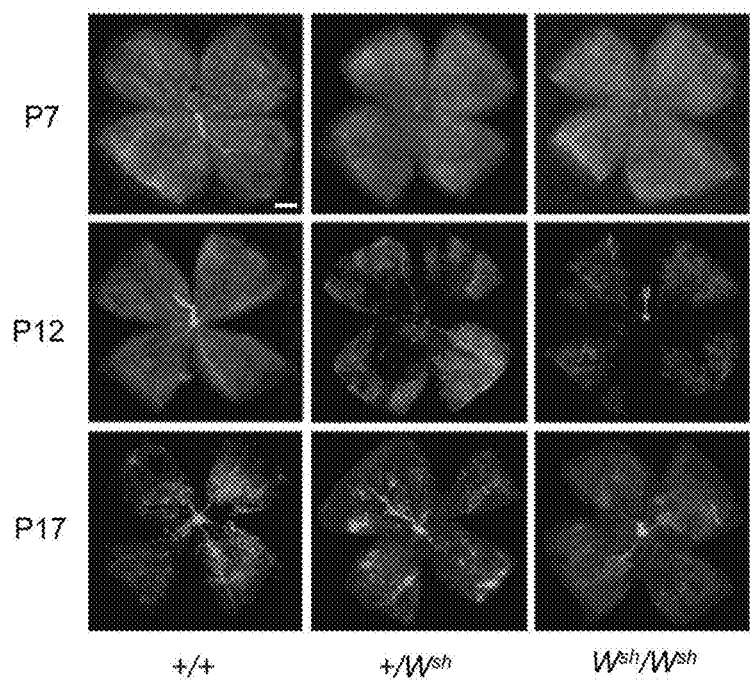
FIG. 1A illustrates fluorescent staining images of sections from retinas of mice in Reference Example 1. It is shown in this Figure that in a whole-mounted retina, pathological neovascularization shown therein as a flux is inhibited in mast cell knockout mice on P17. The scale bar indicates 500 µm.

A therapeutic or prophylactic agent for retinopathy of prematurity (ROP) of the present invention includes at least one compound selected from the group consisting of inhibitors against tryptase derived from a mast cell and mast cell stabilizers as an active ingredient.

Because the therapeutic or prophylactic agent for ROP of the present invention includes inhibitors against tryptase derived from a mast cell and/or mast cell stabilizers as an active ingredient, neovascularization induced by a factor released from a mast cell under a high oxygen concentration condition can be inhibited. A prophylaxis effect or a therapeutic effect against occurrence of ROP can thus be expected.

More specifically, the present invention has been devised based on new knowledge such that the above-described mast cells are deeply involved in the pathogenic mechanism of ROP, not in normal neovascularization or neovascularization related to tumors.

The present invention will be described below.

A term "step" herein not only refers to an independent step but also a step that may not be clearly distinguished from other steps but a purpose intended thereto is achieved.

In addition, a symbol "-" and a term "to" used between numeric values are used to denote a range which includes the numeric values described across the symbol of the term as a minimum value and a maximum value, respectively.

Further, an amount of components included in a composition, if a plurality of substances corresponding to the components are present in the composition, herein refers to a total amount of the plurality of substances present in the composition unless otherwise described.

Therapeutic or Preventive Agent for ROP

The therapeutic or prophylactic agent for ROP of the present invention includes at least one compound selected from the group consisting of inhibitors against tryptase derived from a mast cell and mast cell stabilizers.

Both tryptase inhibitors and mast cell stabilizers can inhibit a substance that is released from a mast cell to contribute to retinal neovascularization from actually starting the neovascularization. Because the therapeutic or prophylactic agent for ROP includes the compounds as active ingredients, promotion of neovascularization caused by mast cells in the retina when ROP has occurred is inhibited and occurrence and development are inhibited.

The therapeutic or prophylactic agent for ROP may include either one of the tryptase inhibitor and the mast cell stabilizer alone or may include a combination of two or more of them.

Tryptase is a serine proteinase derived from secretory granules and included in mast cells as the most abundant proteinase. Tryptase derived from mast cells is already known (Proc. Natl. Acai. Sci. 87, 3811-3815 (1990)) and cleaves a protein with an arginine residue and a lysine residue.

The tryptase inhibitor is not particularly limited and any substance can be used that is capable of inhibiting tryptase from exhibiting physiological activity after tryptase is released from a mast cell in the retina, such as nafamostat mesilate (NM), APC-366 (CAS REGISTRY NO: 178925-65-0, N-(1-hydroxy-2-naphthoyl)-L-arginyl-L-prolinamide hydrochloride, a free form of CAS REGISTRY NO 158921-85-8), APC-2059 (CRA-2059) (CAS REGISTRY NO: 433337-07-6), AVE-5638 (CAS REGISTRY NO: 1032129-37-5), AVE-8923 (CAS REGISTRY NO: 1032129-43-3), RWJ-56423 (CAS REGISTRY NO: 287182-50-7,2-pyrrolidinecarboxamide, 1-acetyl-N-[(1S)-4-[(aminoiminomethyl) amino]-1-(2-benzothiazolylcarbonyl)butyl]-4-hydroxy-, (2S,4R)-(CA INDEX NAME)), RWJ-58643 (CAS REGISTRY NO: 287183-00-0,2-pyrrolidinecarboxamide, 1-acetyl-N-[4-[(aminoiminomethyl)amino]-1-(2-benzothiazolylcarbonyl)butyl]-4-hydroxy-, (2S,4R)-(CA INDEX NAME)), tryptase inhibitors such as lactoferrin and pharmaceutically acceptable salts thereof, peptide derivatives having an anti-tryptase activity and anti-tryptase antibodies, peptide/protein or nucleic acid molecules that inhibit tryptase activity such as aptamers, and inhibiting factors inhibiting generation and functions of tryptase genes such as siRNA and miRNA, including antisenses targeting tryptase DNAs and mRNAs.

The anti-tryptase antibody having anti-tryptase activity (hereinafter simply referred to as an "anti-tryptase neutralizing antibody") is not particularly limited and either a known polyclonal antibody or monoclonal antibody can be used. It is preferable if the antibodies be an antibody which neutralizes tryptase of the species to be targeted. The anti-tryptase neutralizing antibody may be a polyclonal antibody, which is obtained by immunizing an animal other than the targeted species with tryptase of the targeted species, or a monoclonal antibody obtained from hybridoma produced by fusioning a splenic cell of the animal with an immortalized cell. The neutralizing antibody like this can be produced by a general method based on ordinary knowledge of a person skilled in the art. Examples of commercial antibodies that neutralize human tryptase include antibodies such as Human Tryptase beta-2 MAb (Clone 349414) Mouse IgG1 (R&D systems, Cat. No. MAB37961).

The tryptase inhibitor may be used in an amount effective for therapy or prophylaxis of ROP, and the amount effective for therapy or prophylaxis may be 0.01 mg/day to 500 mg/day per postnatal weight (kg) of the individual.

For the mast cell stabilizer, any substance that inhibits degranulation of the mast cell may be employed. The mast cell stabilizer of the present invention also includes a substance which has not only activity for inhibiting degranulation of a mast cell but also another bioactivity such as antihistaminic action. Examples of the mast cell stabilizer like this include substances such as cromoglycic acid (cromolyn), pemirolast, amlexanox, tranilast, acitazanolast, ibudilast, repirinast, tazanolast, suplatast, picumast, tioxamast, quinotolast, andolast, nedocromil, tagorizine, AM-3301 (ME-3301), TA-5707 (CAS REGISTRY NO: 83282-09-1, 2-pyridinecarboxamide, 6-methyl-N-2H-tetrazol-5-yl-, sodium salt (1:1) (CA INDEX NAME), a free form of CAS REGISTRY NO 83282-08-0), batebulast, quazolast, AL-136 (KP-136) (CAS REGISTRY NO: 76239-32-2, 8-(hexyloxy)-3-(1H-tetrazol-5-yl)coumarin)doqualast, MAR-99 (CAS REGISTRY NO: 98772-05-5, 5-pyrimidinecarboxylic acid, 1,6-dihydro-2-[[2-(two-methylpropoxy)phenyl]amino]-6-oxo-(CA INDEX NAME)), asobamast, AS-35 (CAS REGISTRY NO: 108427-72-1, 4H-pyrido[1,2-a]pyrimidin-4-one, 9-[(4-acetyl-3-hydroxy-2-propylphenoxy)methyl]-3-(2H-tetrazol-5-yl)-(CA INDEX NAME), HSR-6071 (PTPC) (CAS REGISTRY NO: 111374-21-1, 2-pyrazinecarboxamide, 6-(1-pyrrolidinyl)-N-2H-tetrazol-5-yl-(CA INDEX NAME)), AHR-5333B (CAS REGISTRY NO: 60284-71-1, ethanone, 1-[4-[3-[4-[bis(4-fluorophenyl)hydroxymethyl]-1-piperidinyl]propoxy]-3-methoxyphen yl]-(CA INDEX NAME)), CI-949 (CAS REGISTRY NO: 121530-58-3, L-arginine, compd. with 5-methoxy-3-(1-methylethoxy)-1-phenyl-N-2H-tetrazol-5-yl-1H-indole-2-carboxamide (1:1) (CA INDEX NAME), a free form of CAS REGISTRY NO 104961-19-5), tetrazolast, acreozast, CI-959 (CAS REGISTRY NO: 104795-68-8, benzo[b]thiophene-2-carboxamide, 5-methoxy-3-(1-methylethoxy)-N-2H-tetrazol-5-yl-, sodium salt (1:1) (CA INDEX NAME), a free form of CAS REGISTRY NO 104795-66-6), crompro-xate, LCB-2183 (CAS REGISTRY NO: 158454-08-1), Zy-15106 (CAS REGISTRY NO: 3106-85-2), N-acetyl aspartyl glutaminic acid), bamaquimast, CGP-25875 (6-butyryl-1-ethyl-4-hydroxy-7-methyl-2-oxo-1,2-dihydroquinoline-3-carboxylic acid), PNU-142731A (CAS REGISTRY NO: 214212-38-1), ethanone, 2-(2,4-di-1-pyrrolidinyl-9H-pyrimido[4,5-b]indol-9-yl)-1-(1-pyrrolidinyl)-, hydrochloride (1:1) (CA INDEX NAME), free form of CAS REGISTRY NO 214212-39-2): doxantrazole (doxantrol), oxatomide, olopatadine, elbanizine, noberastine, FAHF-2 (Food Allergy Herbal Formula-2), mequitazine, ketotifen, azelastine, astemizole, terfenadine, emedastine, epinastine, ebastine, cetirizine, fexofenadine, bepostatine besilate, levocabastine, loratadine, and levocetirizine. These substances may also be in a form of a salt, such as a sodium salt and a potassium salt, and a form of an isomer, and further may be in a form of a solvate such as a hydrate.

The mast cell stabilizer may be used in an amount effective for the therapy or prophylaxis of ROP, and the amount effective for therapy or prophylaxis may be 0.0001 mg/day to 500 mg/day per postnatal weight (kg) of the individual. A preferable dose differs for different mast cell stabilizer and can be determined according to results of nonclinical tests or clinical tests by the skilled person. For example, a preferable dose for a case of using sodium cromoglicate as the mast cell stabilizer may be 0.01 mg/day to 100 mg/day per postnatal weight (kg) of the individual, for example.

Active ingredients of the therapeutic or prophylactic agent, which is at least one compound selected from the group consisting of the inhibitors against tryptase derived from a mast cell and the mast cell stabilizers, can be administered alone or mixed with various pharmaceutically acceptable pharmaceutic aids and in a form of a pharmaceutical composition, pharmaceutical preparation, and the like. Preferably, it may be in a form of a pharmaceutical preparation suitable for use by oral administration, parenteral administration, or the like.

Examples of the parenteral administration include instillation, intravitreal administration, subconjunctival administration, administration under the Tenon's capsule, intracameral administration, intranasal administration, airway administration, percutaneous administration, intravenous administration, intramuscular administration, subcutaneous administration, percutaneous administration, intraperitoneal administration, or the like.

Examples of the form of the pharmaceutical preparation include a solution preparation, a dispersion preparation, a semisolid preparation, a particulate preparation, a molded preparation, and effusion preparation, such as a tablet, a coated tablet, a preparation coated with sugar, a pill, a troche, a hard capsule, a soft capsule, a microcapsule, an implant, an epipastic, a powdered preparation, a granular preparation, a fine grain preparation, an injectable, a liquid medicine, an elixir, an emulsion, an irrigation formulation, a syrup preparation, a pharmaceutical solution, a milk, a suspension preparation, a liniment, a lotion, an aerosol, a spray, an inhalant, a propellant, an ointment formulation, a plaster preparation, a patch, a paste, a poultice preparation, a cream, an oil solution, an eye drop, a nasal drop, an ear drop, a balm, an infusion, a powder drug for a liquid medicine for injection and the like, a freeze-dried preparation, and a gel preparation.

The pharmaceutical composition can be formulated according to an ordinary method. For example, the pharmaceutical composition can be produced by using the following preparations alone or as a mixture of two or more of them, appropriately and where necessary, together with tryptase inhibitors or mast cell stabilizers, and in a unit dosage form required for generally accepted implementation of formulations: a physiologically acceptable carrier, a pharmaceutically acceptable carrier, an adjuvant, a diluent, an excipient, a thinner, a flavoring agent, a perfume material, a sweetening agent, a vehicle, a preservative, a stabilizing agent, a binding agent, a pH regulator, a buffer, a surfactant, a base, a solvent, a filler, an extender, a solubilizer, a solubilizing agent, an isotonizing agent, an emulsifier, a suspending agent, a dispersant, a thickener, a gelling agent, a curing agent, an absorbent, an adhesive, an elasticizer, a plasticizer, a disintegrator, a propellant, a preservative, an antioxidant, a sunproofing agent, a moisturizer, a mitigator, an antistatic agent, an analgesic agent, and the like.

Examples of the preparations suitable for parenteral use includes an aseptic solution of an active ingredient and water or other pharmaceutically acceptable media, or a suspension agent such as an injectable. Example of a referable liquid carrier for injectables generally include water, saline, an aqueous solution of dextrose, a solution of other related sugar, ethanol, glycols such as propylene glycol and polyethylene glycol. The injectable can be prepared into an injectable form, such as a solution, a suspension, or an emulsion, by a method known in the field, by using carriers such as distilled water, Ringer's solution, and physiological saline, an appropriate dispersant or a humidifying agent, and a suspending agent.

An aqueous liquid for injection includes physiological saline, an isotonic solution including glucose and other adjuvants (e.g., D-sorbitol, D-mannitol, sodium chloride, and the like), for example, and may further contain appropriate pharmaceutically acceptable solubilizer, such as alcohol (ethanol and the like), polyalcohol (propylene glycol, polyethylene glycol, etc.), an nonionic surfactant (polysorbate 80 and the like).

Examples of oily liquids for injection include sesame oil, soybean oil and the like, and the liquid may further include benzyl benzoate, benzyl alcohol, and the like as a solubilizer. The liquid may be combined with a buffer agent (a phosphate buffer solution, a sodium acetate buffer solution, etc.) or a reagent for osmotic regulation, an analgesic agent (benzalkonium chloride, procaine hydrochloride, etc.), a stabilizer (human serum albumin, polyethylene glycol, etc.), a preservative (benzyl alcohol, phenol, etc.), an antioxidant such as ascorbic acid, and an absorption promoter. The prepared injection liquid is usually charged into an appropriate ampoule.

The therapeutic or prophylactic agent for ROP according to the present invention can exhibit a therapeutic or prophylactic effect against ROP by administering the same to postnatal individuals.

Examples of the subject of administration of the therapeutic or prophylactic agent for ROP may include subjects that can develop ROP, not only humans but also other mammals such as dogs, rats, mice, rabbits, cats, ferrets, and guinea pigs, but not particularly limited thereto.

The time of dose of the therapeutic or prophylactic agent for ROP is different for different species and different states of the subject of administration.

If a mammal other than humans is the subject, the time of dose can be a time period from immediately after birth of the subject to the seventh day after birth.

If the subject is a human, particularly if the subject is a human infant with very low birth weight or the like and is subjected to a high oxygen concentration environment for a specific time period immediately after birth, it is preferable to administer the therapeutic or prophylactic agent for ROP starting from a timing in which the subject has entered the high oxygen concentration environment or some time earlier than the environment shift (e.g., the day before the environment shift), or starting from the timing of start of reduction of the oxygen concentration of the subject's environment or a timing of environmental shift to a normal oxygen environment or some time earlier than these timings (e.g., the day before the environment shift or oxygen concentration reduction).

The term "normal oxygen environment" herein refers to an environment in which the percentage content of oxygen is approximately 21.0 vol. % of the entire atmosphere. Note that the normal oxygen environment may be a normal indoor environment (at room air). The term "high oxygen concentration environment" herein refers to an environment with the oxygen concentration higher than that of the "normal oxygen environment and preferably refers to an environment with a high oxygen concentration continuously or temporarily provided in order to support and control the life of an infant with very low birth weight, and it is preferable if the percentage content of oxygen be 30 to 100 vol. %. Also in a case where an infant with very low birth weight who has been subjected to the high oxygen concentration environment is to undergo an environment with a higher oxygen concentration because of the need for support and control the life of the infant, the therapeutic or prophylactic agent of the present invention can be administered.

In addition, if the subject infant has been subjected to the high oxygen concentration environment for a specific period immediately after birth and if the arterial oxygen saturation has been monitored, the therapeutic or prophylactic agent of the present invention can be administered by using the arterial oxygen saturation as an index. In this case, in the monitoring of the arterial oxygen saturation, an apparatus can be used which measures the oxygen saturation in blood noninvasively and with time, such as a pulse oximeter.

In administering the therapeutic or prophylactic agent of the present invention by using the arterial oxygen saturation as an index, the therapeutic or prophylactic agent of the present invention can be administered if high arterial oxygen saturation is to be maintained, if it is necessary to temporarily raise the arterial oxygen saturation to a level higher than the saturation currently maintained, if the arterial oxygen saturation has risen to a level higher than the target level of the maintenance due to some causes, or the like. In these cases, it is preferable to administer the therapeutic or prophylactic agent of the present invention if the arterial oxygen saturation is higher than 85% and 100% or lower, preferably higher than 90% and 100% or lower, more preferably higher than 93% and 100% or lower, and yet more preferably higher than 95% and 100% or lower. For the administration of the agent, it is preferable to administer the therapeutic or prophylactic agent for ROP starting from the timing of increase of the arterial oxygen saturation or some time earlier than the timing (e.g., the day before the timing), or alternatively, starting from the timing of start of reduction of the arterial oxygen saturation or some time earlier than the timing (e.g., the day before the timing).

The period of dose of the therapeutic or prophylactic agent for ROP is a time period until the therapy or the prophylaxis is accomplished, and for human infants with very low birth weight, the period of dose of the agent may be until a timing at which it is determined that the possibility of occurrence of ROP has become low, such as a time period continued until a timing at which the weight of the subject exceeds 2,000 g or a time period continued until a timing at which formation of normal retinal capillary is observed by examination of the fundus, although the time period differs depending on the environment or the state in which respective individual patients are in, such as the respective lengths of the time period in which the subject is subjected to the high oxygen concentration environment and the time period in which the subject is subjected to the normal oxygen environment, variation of the oxygen concentration in the high oxygen concentration environment, and variation of the arterial oxygen saturation. In order to suppress side effects, the period of dose can be a period of 5 to 10 days, preferably 7 to 8 days, starting from the timing of environmental shift from the high oxygen concentration environment to the normal oxygen environment or the timing of start of reduction of the oxygen concentration from the high oxygen concentration environment, or from the timing in which the arterial oxygen saturation has been reduced or from the timing of start of the reduction of the arterial oxygen saturation. Also in the case where the subject has been temporarily subjected to the high oxygen concentration environment, where air with an especially high oxygen concentration has been given under the high oxygen concentration environment, or where the subject has been temporarily subjected to a state with an especially high arterial oxygen saturation, the period of dose may be 5 to 10 days, preferably 7 to 8 days, after the temporary treatments have been completed, in consideration of reduction of side effects.

Therapy or Prophylaxis for ROP

The present invention also includes a method for therapy or prophylaxis of ROP including administration of the therapeutic or prophylactic agent for ROP to a subject (also referred to herein as a "patient") needing the therapy or prophylaxis of ROP.

In the method for therapy or prophylaxis, the therapeutic or prophylactic agent for ROP suited to the pathogenic mechanism of ROP is administered to a subject needing the administration of the therapeutic or prophylactic agent, and thereby a high therapeutic or prophylactic effect is expected.

For a scope of the subject, time of dose, a dose, and the like of the method for therapy and prophylaxis, the above description thereof are applied as they are.

The method for therapy or prophylaxis of the present invention is preferably applied to an infant with very low birth weight who is subjected to the high oxygen concentration environment that has been continuously or temporarily given in order to support and control the life of the subject, in particular the high oxygen concentration environment in which the percentage content of oxygen is 30 to 100 vol. %, and in this case, the period of dose may be 5 to 10 days, preferably 7 to 8 days, starting from the timing of shift to the high oxygen concentration environment or some time earlier than the environmental shift (e.g., the day before the timing), from the timing of start of reduction of the oxygen concentration from the high oxygen concentration environment, from the timing of shift to the normal oxygen environment or some time earlier than the environmental shift (e.g., the day before the timing), from the timing of shift from the high oxygen concentration environment to the normal oxygen environment, from the timing of start of reduction of the oxygen concentration from the high oxygen concentration environment, or from the timing of start of reduction of the arterial oxygen saturation.

Testing Method for ROP

The testing method for ROP according to the present invention includes detecting a marker substance that can be released by degranulation of mast cells in a biological sample originating from a patient (hereinafter simply referred to as a "detection step") and determining whether the subject has been affected by ROP or whether prophylaxis or therapy of ROP is necessary (hereinafter simply referred to as a "determination step") on the basis of the detected amount of the marker substances.

In the testing method for ROP, whether the patient has been affected by ROP whether prophylaxis or therapy of ROP is necessary is determined on the basis of the detected amount of the marker substance that can be released from mast cells by degranulation thereof, and thus the presence of ROP in a patient, if it is present, or the necessity of prophylaxis or therapy of ROP can be determined accurately and at an early stage on the basis of the pathogenic mechanism.

Examples of the marker substance that can be released by degranulation of mast cells include tryptase, chymase, β-hexosaminidase, VEGF, FGF-2, IL-8, NGF, heparin, TGF-β, TNF-α, histamine, and the like.

For the biological sample used in the detection step, any sample possibly containing a marker substance that can be released by degranulation of mast cells can be used, and examples of biological samples like this include tissue samples from a tissue such as retina, a vitreous body, and a body surface tissue; body fluid samples such as blood, plasma, serum, lymph, and aqueous humor; urine samples; lacrimal fluid; and samples from leukocyte fractions and erythrocyte fractions in blood. It is particularly preferable if the biological sample be blood or plasma considering the ease of collection or detection.

Of the biological samples, tissue samples can be detected by histopathological tests such as immunostaining and by molecular biological processes such as in situ hybridization. For methods of preparing the samples for histopathological tests, frozen sections or paraffin-embedded sections prepared by conventional methods may be used for detection of marker substances. In addition, a tissue may be crushed by general methods such as homogenization and marker components extracted therefrom may be solubilized for use in the detection.

For biological fluid samples and urine samples among the biological samples, samples collected from subjects may be used in states as they are or the samples may undergo pretreatment such as concentration or dilution. The pretreatment of the biological samples can be carried out by ordinary methods.

The detection of marker substances that can be released by degranulation of mast cells can be performed in a known method. The detection will be described below with reference to detection of tryptase as an example.

For the detection of tryptase, detection methods capable of quantification or semi-quantification usually used for detecting proteins can be applied.

The detection method is preferably a detection method by an immunochemical means that uses an antibody recognizing tryptase as a tryptase detection reagent considering the sensitivity, specificity, and convenience of the detection. In addition, detection based on enzyme activity can be performed by using a labeled substrate of tryptase and detecting the released label on the basis of enzyme activity.

Examples of the detection method by the immunochemical means include methods usually performed in the technical field. Examples of the detection method include methods such as enzyme-linked immunosorbent assay (ELISA), chemiluminescence immunoassay, immunochromatography, electrochemiluminescence immunoassay, spectrometry, immunofluorescence, radioimmunoassay (RIA), surface plasmon resonance (SPR), Western blot analysis, and dot blotting, and considering the sensitivity, specificity, and convenience of the detection, it is preferable to use the enzyme-linked immunosorbent assay (ELISA) and immunochromatography.

The antibody recognizing tryptase (hereinafter simply referred to as an "anti-tryptase antibody") is not particularly limited, and either of known polyclonal antibodies or monoclonal antibodies can be used. The antibodies are preferably an antibody recognizing tryptase of the detection target species. The anti-tryptase antibody may be a polyclonal antibody obtained by immunizing an animal other than the detection target species by tryptase of the detection target species or a monoclonal antibody obtained from hybridoma prepared by fusion between splenic cells of the animal with immortalized cells. The antibody like this can be prepared by a general method on the basis of ordinary knowledge of a person skilled in the art. Examples of commercial antibodies recognizing human tryptase include a rabbit-derived anti-human mast cell tryptase polyclonal antibody (a product of Abcam plc.) and an anti-human mast cell tryptase monoclonal antibody (Clone AA1, a product of Calbiochem, Calif., USA). The term "antibody" herein refers to an antibody that specifically recognizes tryptase, and may be an antibody molecule or a portion or a fragment including an antigen recognizing site (e.g., an H-chain, a J-chain, a VL-chain, a VH-chain, and fragments and the like thereof).

For labels used for detecting the anti-tryptase antibody, any known labeling substances may be used, and examples of such labeling substances include enzymes, chemiluminescent substances, electrochemiluminescent substances, and radioactive substances. It is particularly preferable to use an enzyme as the label considering the sensitivity and the convenience of the detection.

The enzyme is not particularly limited, and any enzyme that can be quantified by physical or chemical methods may be used. Examples of such an enzyme include alkaline phosphatase, horseradish peroxidase (HRP), and luciferase.

The method of detecting the label is not particularly limited and any detection methods capable of quantification or semi-quantification may be used, and the detection method can be appropriately selected conforming to the label. Examples of the label detection means include means using absorbance, emission intensity, fluorescence intensity, and radiation counting. By quantifying or semi-quantifying the labels, tryptase can be quantified or semi-quantified.

The tryptase is preferably tryptase specific to mast cells such as mouse mast cell protease 6 or TPSB2, which is an ortholog thereof.

If β-hexosaminidase is used as the marker substance, similarly to the case of using tryptase, the detection method capable of quantification and semi-quantification usually used for detection of proteins is applicable, and the detection is performed preferably by a detection method using an antibody specific to β-hexosaminidase. A detection method based on an enzyme activity described below in Example 5 can also be used.

In the determination step, whether the patient who has provided the biological samples has been affected by ROP or whether the patient is in a state needing prophylaxis or therapy of ROP is determined on the basis of a detected amount of the marker substance that has been detected in the detection step and can be released by degradation of mast cells.

The determination can be performed by comparison between the detected amount described above and a detected amount of the marker substance in a biological sample derived from a healthy subject. Because the amount of marker substances released from mast cells of healthy subjects is smaller than the amount of marker substances released from mast cells of patients with ROP, whether the patient has been affected by ROP or whether the patient is in a state needing prophylaxis or therapy of ROP can be readily determined by comparison with the detected amount of marker substances in the biological sample derived from healthy subjects. As used herein, the term "healthy subject" refers to an individual for whom it has already been clearly known that the individual has not been affected by ROP.

In the determination, in order to distinguish between healthy subjects and individuals with ROP, a normal detection amount may be set and the determination may be performed on the basis of whether the detected amount is larger than the normal detection amount.

If the marker substance is specific to mast cells, or if the marker substance is not detected in samples from healthy subjects, it can be determined that the patient is in a state needing prophylaxis or therapy of ROP according to the detected marker substance.

Because the amount of marker substances released from mast cells increases as the mast cells are activated, it can be determined whether the patient has been affected by ROP or whether the patient is in a state needing prophylaxis or therapy of ROP by comparison between the amounts of the marker substances released from mast cells in an activated state and an inactivated state.

The mast cells may also be tissue-derived mast cells or may be cultured mast cell strains that reflect properties of normal cells.

In addition, in order to distinguish between mast cells in an inactivated state and mast cells in an activated state, a detection amount in the activated state may be set to perform the determination on the basis of whether the detected amount is larger than the detection amount in the activated state.

The normal detection amount or the detection amount in the inactivated state or the detection amount in the activated state can be defined as a value obtained by adding a value 2-3 times the standard deviation to an average value of the amount detected in mast cells of healthy subjects or in the inactive state or in the active state, for example, and can be appropriately set as a value that satisfies the sensitivity or the specificity with an excellent balance.

The testing method for ROP of the present invention can be combined with the therapy or prophylaxis of the ROP described above. In other words, the present invention is a therapy or prophylaxis of retinopathy of prematurity including detecting marker substances that can be released by degranulation of mast cells from biological samples derived from a subject, determining whether the subject is a patient needing therapy or prophylaxis of retinopathy of prematurity on the basis of a detected amount of the marker substances, and administering a therapeutic or prophylactic agent for retinopathy of prematurity that includes at least one compound selected from the group consisting of inhibitors against tryptase derived from mast cells and mast cell stabilizers as an active ingredient to a patient needing therapy or prophylaxis of retinopathy of prematurity by an amount effective for the therapy or prophylaxis therefor.

After having changed the concentration of oxygen of the environment or the arterial oxygen saturation, or after the arterial oxygen saturation has varied, it may be determined whether the patient is in a state needing prophylaxis or therapy of ROP by the testing method for ROP of the present invention and the therapeutic or prophylactic agent of the present invention may be administered by an effective amount if it has been determined that prophylaxis or therapy of ROP is necessary.

Test Kit

A test kit for ROP according to the present invention is an test kit including a reagent for detecting marker substances that can be released by degranulation of mast cells, such as tryptase detection reagents.

According to the test kit, which includes the marker substance detection reagent capable of detecting marker substances that can be released from mast cells in the high oxygen concentration environment, and thereby it can be accurately examined whether the patient has been affected by ROP in an early stage on the basis of the pathogenic pathology thereof.

For the reagent for detecting marker substances included in the test kit, the above-described marker substance detection reagent can be applied as they are.

The marker substance detection reagent may be included as one component of the test kit in a form in which it is stored in a storage portion. The "storage portion" in this kit is not particularly limited as long as the portion is provided in a form effective for allowing respective components to be present independently from one another without being mixed together, and the storage portion may be in the form of a vessel or an individual package, or may be in the form of one sheet that is a region sectioned independently from other portions.

The test kit may include, as well as the marker substance detection reagent, a diluent or a buffer that can be used for preparing the biological sample which may include the marker substance or for controlling the concentration thereof to an appropriate level, and may include, in addition thereto or in substitution therefor, other reagent necessary for measurement, positive or negative control samples, or reagents necessary for preparation thereof. The kit may include a document that includes reference values such as the normal detection amount, the detection amount in the inactive state, and the detection amount in the active state.

Screening Method for the Therapeutic or Preventive Substance for ROP

A screening method of the present invention is a method for screening a therapeutic or prophylactic substance for retinopathy of prematurity including subjecting mast cells to a process of inducing release of marker substances that can be released by degranulation of the mast cells (hereinafter may also be referred to as a "marker substance release induction step"), bringing the mast cells having been subjected to the marker substance release induction process into contact with a candidate substance (hereinafter may also be referred to as a "contacting step"), detecting the marker substance released from the mast cells after the contact (hereinafter may also be referred to as a "marker substance detection step"), and screening, after determining whether the candidate substance has an activity of inhibiting release of the marker substances on the basis of a detected amount of the marker substances, the candidate substance having been determined to have a marker substance release inhibiting activity as a target substance capable of exhibiting a therapeutic or prophylactic effect for retinopathy of prematurity (hereinafter may also be referred to as a "screening step").

In the screening method, detection of the marker substances released from the mast cells having been subjected to the marker substance release induction process is performed and substances having the marker substance release inhibiting activity are screened as target substances on the basis of the detected amount of the obtained marker substances, and thereby target compounds that can exhibit an effect of therapy or prophylaxis of ROP, for which release of marker substances from mast cells has been proven to be involved in the occurrence of ROP, can be highly efficiently screened.

In the marker substance release induction step, mast cells are subjected to the marker substance release induction process.

The mast cells used in the marker substance release induction step may be mast cells having been induced from naturally derived mast cells or precursor cells of naturally derived mast cells in vitro, or may be cultured mast cell strains. If natural mast cells are used, the mast cells may be mast cells derived from a living body or may be mast cells present inside an individual. In other words, the marker substance release induction process may be an in vivo process that uses an individual per se, and may be an in vitro process that uses mast cells.

The origin of the mast cells is not particularly limited, and examples thereof include primate animals such as humans and monkeys; rodents such as mice and rats, and rabbits; dogs; and cats. Considering the ease of availability, if an individual per se is used in the marker substance release induction process, it is preferable if the mast cells be mast cells of mice, rats, rabbits, or the like. If cultured mast cell strains are used for the marker substance release induction process, it is preferable if the origin of the mast cell strains be humans, mice, rats, rabbits, or the like.

The above-described mast cells may be cells obtained by culturing precursor cells of mast cells such as bone marrows separated from a living body or cord blood-derived monocytes in the presence of appropriate cytokines such as interleukin-3 or stem cell factors for 3 weeks or longer, or alternatively may be mast cell strains available as MC/9 (ATCC CRL-8306), P815 (ATCC TIB-64), and HMC-1.

The marker substance release induction process may be a process in which marker substances are released in a retina, and examples of the marker substance release induction process include retention in the high oxygen concentration environment and the normal oxygen environment subsequent thereto, by cross-linking of IgE receptors by an IgE-antigen complex, or by exposure to substances that induce macrophage activation or degranulation, such as calcium ionophore and Compound 48/80. If the mast cells are individual-derived cells or cultured cells, the marker substance release induction process is preferably the retention in the high oxygen concentration environment and the normal oxygen environment subsequent thereto considering involvement with the pathogenic mechanism of ROP. For the high oxygen concentration environment and the normal oxygen environment, the above descriptions are applied as they are.

For a period of retention in the high oxygen concentration environment, it is preferably 5 days or longer on the in vivo level and 12 hours or longer on the in vitro level considering secured induction of release of marker substances such as tryptase. For a period of retention in the normal oxygen environment coming subsequent to the high oxygen concentration environment, it is preferably 5 days or longer on the in vivo level and 12 hours or longer on the in vitro level.

The retention of mast cells in the normal oxygen environment may be performed under conditions usually applied for maintaining cells derived from individuals or cultured cells. If the mast cells are individual-derived cells, they can be retained in the normal oxygen environment of 20.0-26.0° C. with the relative humidity of 30.0-70.0%. If cultured mast cells are to be retained, they can be retained in a culture solution such as a DMEM medium, an RPMI1640 medium, or an α-MEM medium supplemented with serum components where necessary, under conditions of 37° C., 5 v/v % $CO_2$.

In the contacting step, the mast cells having been subjected to the marker substance release induction process are brought into contact with candidate substances. The method of contact among the mast cells and the candidate substances is not particularly limited, and the contact may be performed in an environment in which the retention of the mast cells is not impaired. Examples of such a contact include: oral administration or parenteral administration with a reagent including the candidate substance on the in vivo level; and cultivation using a culture solution including the candidate substance on the in vitro level.

If the contact among the mast cells and the candidate substances is carried out on the in vivo level, it is preferable if the candidate substance administered ex vivo contact the mast cells existing in vivo immediately at the timing of the release induction process. The optimum administration start timing may differ in some cases depending on the administration method and dynamics of the candidate substances in vivo, and it is generally preferable to start administration of the candidate substance at a timing 1 day before the release induction process or around. It is also preferable to keep the contact among the mast cells and the candidate substances throughout the test period considering secured contact among the mast cells and the candidate substances. If the contact between the mast cells and the candidate substances is to be performed on the in vitro level, it is preferable if the mast cells are brought into contact with the candidate substances at the timing of the release induction process, and it is also preferable, considering secured contact among the mast cells and the candidate substances, to keep the contact among the mast cells and the candidate substances before the release induction process, for example throughout the test period.

In the marker substance detection step, detection of the marker substances is performed for the mast cells that have undergone the contact. For the marker substances, the marker substances described above in the section of "Testing Method for ROP" can be used. The detection of the marker substances can be performed by a known method. The preparation of samples used for detection of the marker substances is different for different types of mast cells, and if the mast cells derived from individuals are used, biological samples that can be applied to the test are collected and the collected samples can be used in performing the marker substance detection method. If the mast cells are cultured mast cells, the culture solution retaining the cultured mast cells and the mast cells that have been cultured where necessary are recovered and subjected to the marker substance detection method. For the detection using tryptase or β-hexosaminidase as the marker substance, the above description about the detection method for tryptase and β-hexosaminidase described about the detection method for ROP can be applied as they are.

In the screening step, substances having the marker substance release inhibiting activity are screened from among the candidate substances as target substances that can exhibit a therapeutic or prophylactic effect for ROP on the basis of the detected amount of the marker substances. Specifically, substances with which the detected amount of the marker substances is reduced compared with the detected amount of the marker substances obtained when the control substances are used may be identified as target substances that can exhibit a therapeutic or prophylactic effect for ROP, and candidate substances with which the detected amount of the marker substances is not reduced by the above comparison may be identified as non-target substances.

In other words, if the detected amount of marker substances is reduced for a specific candidate substance when compared with other substances that do not have a therapeutic or prophylactic activity for ROP, then it is considered that release of marker substances from the mast cells can be inhibited in terms of occurrence of ROP, and thus the specific candidate substance described above may possibly become a therapeutic or prophylactic substance for ROP.

According to the screening method, substances having a therapeutic or prophylactic effect for ROP can be highly efficiently screened by using a simple and convenient index of inhibition of release of marker substances that can be released by degranulation of mast cells.

EXAMPLES

The present invention will be described in detail below with reference to examples. However, the present invention is not limited by the examples at all. The unit "%" herein refers to percentage by mass unless otherwise noted.

Reference Example 1

(1) Neovascularization in Mast Cell Knockout Mice
(a) Preparation of Model Mice

Mast cell knockout mice C57BL/6-$W^{sh}/W^{sh}$ mice (hereinafter simply referred to as "$W^{sh}/W^{sh}$ mice"), mast cell non-knockout mice C57BL/6-+/+ mice (hereinafter referred to as "+/+ mice"), and heterozygote mice thereof C57BL/6-+/$W^{sh}$ mice (hereinafter referred to as "+/$W^{sh}$ mice") were obtained from the BioResource Center of Riken Institute of Physical and Chemical Research. All animal experiments were performed in conformity with the animal experiment guideline by Tokyo University of Agriculture and Technology. The $W^{sh}/W^{sh}$ mice were gene-modified mice known as mast cell knockout mice (Blood 80, 1448-1453 (1992)).

(b) Induction of ROP

As have been reported before (Invest. Ophthalmol. Vis. Sci., 35, 101-111 (1994), etc.), for the +/+ mice, +/$W^{sh}$ mice, and $W^{sh}/W^{sh}$ mice, respectively, neonatal mice were placed in a closed chamber containing 75 v/v % $O_2$ together with their mother for lactation on P7, and this state was maintained for 5 days (P7-P12). Subsequently, this state was continued for further 5 days (P12-P17) in the normal oxygen environment (21 v/v % $O_2$) for induction of oxygen-induced retinopathy (OIR) for use as experimental ROP models. The control mice were raised in the normal oxygen environment (indoor environment, 25° C., 21 v/v % $O_2$. The same applies for the description of Examples.) throughout the test period. Note that the symbol "P", which refers to a date, herein denotes that the date is a postnatal date, and "P7", for example, refers to a 7th postnatal date.

(c) Evaluation of Retinal Neovascularization

The mice were slaughtered on P7, P12, P17, or P25. Whole mount analyses were carried out as have been reported before. To put it briefly, eyes were collected from the mice and then were fixed with 4% paraformaldelyde for 1 hour. Retinas were sectioned and stained with Alexa fluor 488-conjugated G simplicifolia isolectin B4 (a product of Molecular Probes, Inc.) overnight. Flat mounts of the retinas were prepared, fluorographs were taken at the magnification 4, and layered by using the BIOREVO system (a product of Keyence Corp.).

(d) Histologic Examination and Immunohistochemical Examination

On P17, eyes were collected from the mice with ROP, fixed with Davidson's fixative overnight, and then embedded with paraffin. Paraffin-embedded serial sections axially sectioned at 6 μm were obtained, stained with HE, images were taken at the magnification 20, and the number of nuclei of the endothelial cells on the side of the vitreous body of the internal limiting membrane was counted. In the immunohistochemical test, the sections were subjected to incubation at 4° C. overnight together with anti-PECAM-1 antibody (a product of Santa Cruz Biotechnology, Inc.) having been diluted at 1:100 (in capacity ratio).

Differences between the numbers of the nuclei of the endothelial cells for each section were compared by one-way analysis of variance and then by Tukey's test or Fisher's exact test. P values less than 0.05 were considered statistically significant. All the data are shown as mean±SEM.

(e) Results

Because ROP is easily induced in neonatal mice by shifting from the high oxygen concentration environment to the normal oxygen environment, the severity of retinal neovascularization in the mast cell knockout $W^{sh}/W^{sh}$ mice, the mast cell non-knockout +/+ mice, and the heterozygote mice thereof ($+/W^{sh}$) were examined (FIG. 1). After having exposed to the high oxygen concentration environment (P7-P12) for 5 days, vascular retraction was observed by whole mount analysis in the retinal center in all the mice on P12. As have been reported before (Invest Ophthalmol Vis Sci 35, 101-111 (1994), etc.), influences from the high oxygen concentration environment appeared mainly in the capillaries adjacent to artery in the retinal center. By staining the blood vessels, germination of blood vessels being newly formed was observed in the retinas of the +/+ mice on P17. Due to the vascular germination, the capillary plexus was not successfully regenerated, and neovascular tufts were formed toward the vitreous body as characteristic to ROP in human pathology (FIG. 1A).

Figure 1B:
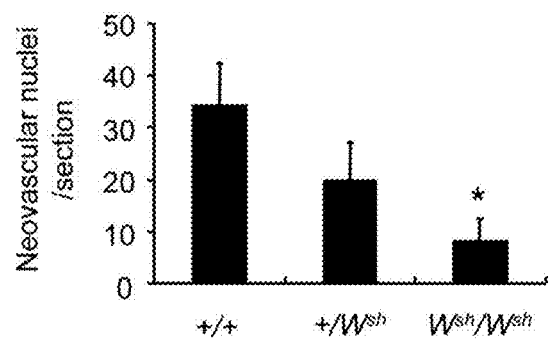
FIG. 1B is a graph illustrating results of evaluation of neovascularization in the mice in Reference Example 1. The retinal neovascularization on P17 was quantified by counting the number of nuclei of neovascular cells on the inner side of the retina of an ocular section after hematoxylin-eosin (HE) staining. The number of neovascular nuclei was smaller for $+/W^{sh}$ mice and $W^{sh}/W^{sh}$ mice compared with $+/+$ mice. The number n=5-6. The sign "*" denotes P<0.05 (compared with the $+/+$ mice). Mean: ±SEM.
Figure 1C:
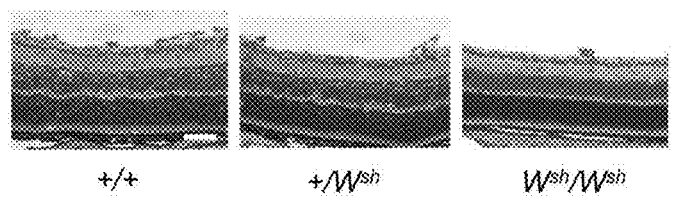
FIG. 1C illustrates HE staining images that shows results of histologic tests on the mice in Reference Example 1. The analysis of retinal section was performed by HE-staining of formalin-fixed paraffin-embedded sections. The scale bar indicates 100 µm.
Figure 1D:
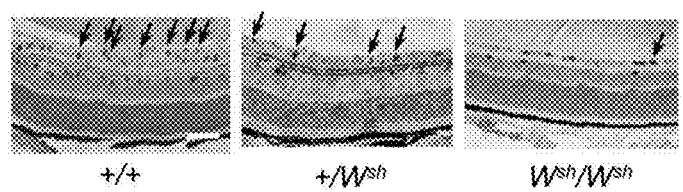
FIG. 1D illustrates staining images showing results of immunohistochemical tests on the mice in Reference Example 1. The analysis of retinal sections was performed by platelet endothelial cell adhesion molecule-1 (PECAM-1) staining of formalin-fixed paraffin-embedded sections. Arrows indicate endothelial cells intruding into the space of the vitreous body. The scale bar indicates 100 µm.

The region of abnormal neovascular chamber was smaller in the $W^{sh}/W^{sh}$ and $+/W^{sh}$ mice compared with that in the +/+ mice; the number of the neovascular nuclei was significantly smaller for the $W^{sh}/W^{sh}$ mice compared with that in the +/+ mice, while in the $+/W^{sh}$ mice, the number of the neovascular nuclei was a value between the values for the other mice (FIGS. 1B and 1C). Intrusion of the platelet endothelial cell adhesion molecule-1 (PECAM-1)-positive endothelial cells into the vitreous body was also very little in the $W^{sh}/W^{sh}$ mice (FIG. 1D).

During the test period, abnormal retinal neovascularization was not observed in all the mice exposed only to the normal oxygen environment (data not illustrated). Accordingly, in order to examine whether retinal neovascularization could be induced due to long-term exposure to the high oxygen concentration environment, +/+ neonatal mice were raised at the oxygen concentration of 75% for 10 days (P7-P17). As a result, capillary loss in the retinal center was observed, but no neovascular chambers were observed as of P17 (data not illustrated).

Reference Example 2

Involvement of mast cells in retinal neovascularization was examined as follows.

Bone marrow-derived cultured mast cells (BMCMC) were isolated from the +/+ mice according to a known method (J Exp Med 174, 7-14 (1991)). The mast cells were cultured for more than 5 weeks according to an ordinary method, then after a cell suspension of which the number of cells were controlled to $1 \times 10^6$ cells/20 μL was prepared, the cell suspension was injected to $W^{sh}/W^{sh}$ neonatal mice on P1 or P2 by intraperitoneal injection by an amount of 20 μL (n=4-6). 20 μL saline was injected to the neonatal mice of the control group by intraperitoneal injection. Subsequently, similarly to Reference Example 1, the mice were slaughtered on P7, P12, P17, or P25, and further, PECAM-1-positive endothelial cells in the newly formed vessels extended into the vitreous body were recovered from the BMCMC-injected $W^{sh}/W^{sh}$ mice. Evaluation, histologic tests, and immunohistochemical tests of retinal neovascularization were performed in the similar manner as Reference Example 1. The results are illustrated in FIG. 2.

Figure 2A:
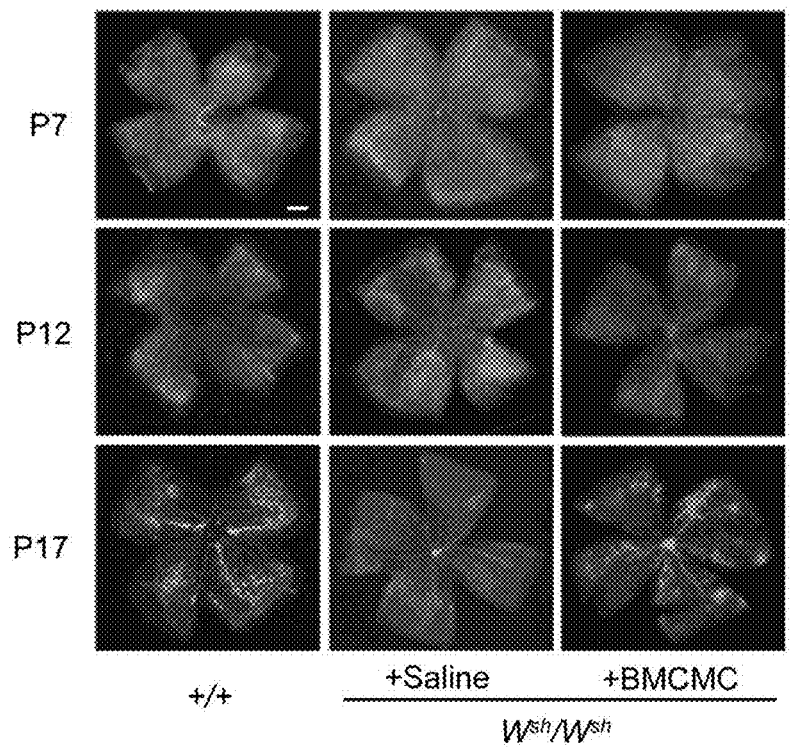
FIG. 2A illustrates HE staining images showing results of administration of bone marrow-derived cultured mast cells (BMCMC) of the mice in Reference Example 2. The BMCMC process revived abnormal neovascularization in the mast cell knockout mice affected by oxygen-induced retinopathy on P17. The scale bar indicates 500 µm.
Figure 2B:
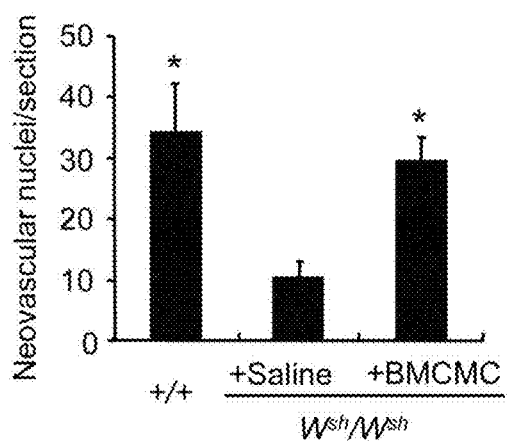
FIG. 2B is a graph which illustrates evaluation results of neovascularization in the mice in Reference Example 2. The retinal neovascularization on P17 was quantified by counting the number of nuclei extended in the HE-stained vitreous body. The number of neovascular nuclei in neonatal mice of the BMCMC-injected $W^{sh}/W^{sh}$ mice was compared with that in the $+/+$ mice. The number n=4-6. The sign "*" denotes P<0.05 (compared with saline-injected $W^{sh}/W^{sh}$ mice). Mean: ±SEM.

In FIG. 2B, the sign "*" denotes P<0.05 (comparison with the results for the saline-injected $W^{sh}/W^{sh}$ neonatal mice). The statistical significance was determined by one-way analysis of variance and Tukey's test. Error bars denote SEM. Scale bars in FIGS. 2C and 2D denote 100 μm.

Figure 2C:
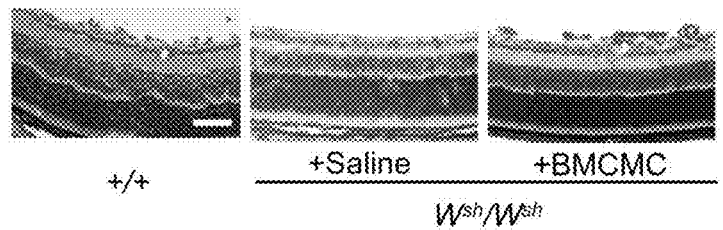
FIG. 2C illustrates HE-staining images showing results of the histological tests on the mice in Reference Example 2. The analysis of retinal sections was carried out by HE staining of formalin-fixed paraffin-embedded sections. The scale bar indicates 100 µm.
Figure 2D:
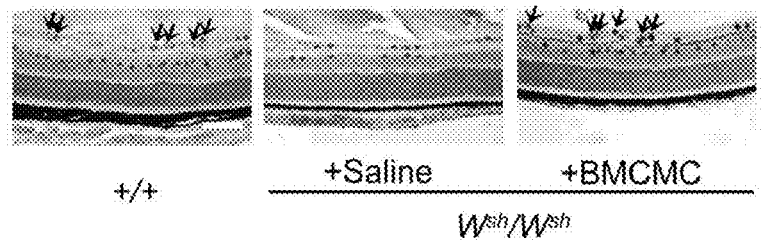
FIG. 2D illustrates staining images showing results of immunohistochemical tests on the mice in Reference Example 2. The analysis of retinal sections was performed by PECAM-1 staining of formalin-fixed paraffin-embedded sections. The scale bar indicates 100 µm.

Retinal neovascularization equal to that in the +/+ mice was observed in the BMCMC-injected $W^{sh}/W^{sh}$ mice on P17, while the saline-injected $W^{sh}/W^{sh}$ mice showed no retinal neovascularization (FIG. 2A). In accordance with this finding, it was clarified from the results of hematoxylin-eosin (HE) staining on the ocular sections that the number of nuclei of the endothelial cell, or the index of variation of neovasculars, was larger for the BMCMC-injected $W^{sh}/W^{sh}$ mice compared with the mice to which saline only was injected (FIGS. 2B, 2C). In addition, the PECAM-1-positive endothelial cells present in the neovasculars extended into the vitreous body were recovered in the BMCMC-injected $W^{sh}/W^{sh}$ mice.

In order to verify the visual functions of the mice used in the above tests, single-signal flash electroretinogram (ERG) patterns on P19 were analyzed.

After allowing the mice to be adapted to darkness overnight, the mice were anesthetized. Contact lens electrodes (a product of Mayo Corporation, N1530NNC) was placed on the eyes, and the reference electrode and the ground electrode were arranged inside the mouth and on the tail, respectively. ERG was recorded by an ordinary test and by using an electrophysiological apparatus (UTAS E-3000: a product of LKC Technologies, Inc.). The results are illustrated in FIG. 3.

Figure 3:
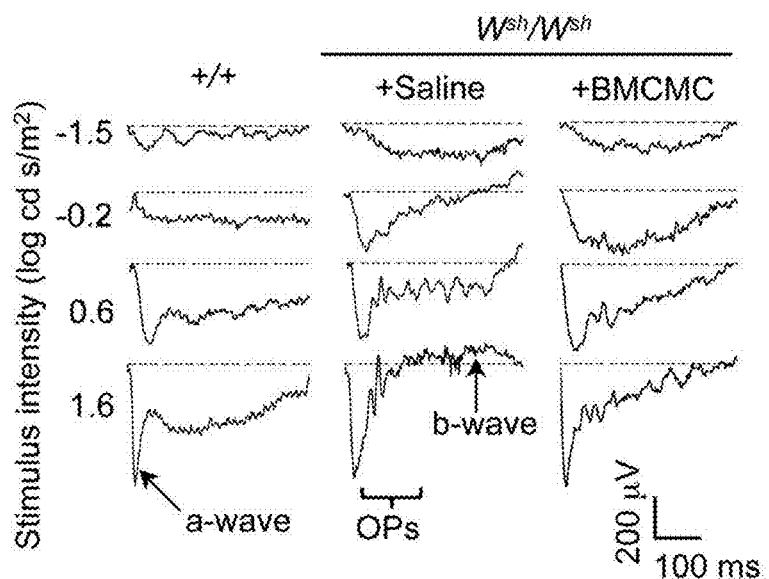
FIG. 3 is a drawing which illustrates electroretinogram patterns in Reference Example 2. In the saline-injected $W^{sh}/W^{sh}$ mice, normal ERG responses on P19 were observed, while in the $+/+$ or BMCMC-injected $W^{sh}/W^{sh}$ no normal ERG response on P19 was observed.

As shown in FIG. 3, the amplitude of OP waves decreased in the +/+ mice and the BMCMC-injected $W^{sh}/W^{sh}$ mice used as ROP models, and the b waves were completely lost. On the other hand, it was clarified that for the $W^{sh}/W^{sh}$ mice to which saline only was injected, the amplitude was normal.

Reference Example 3

Figure 4:
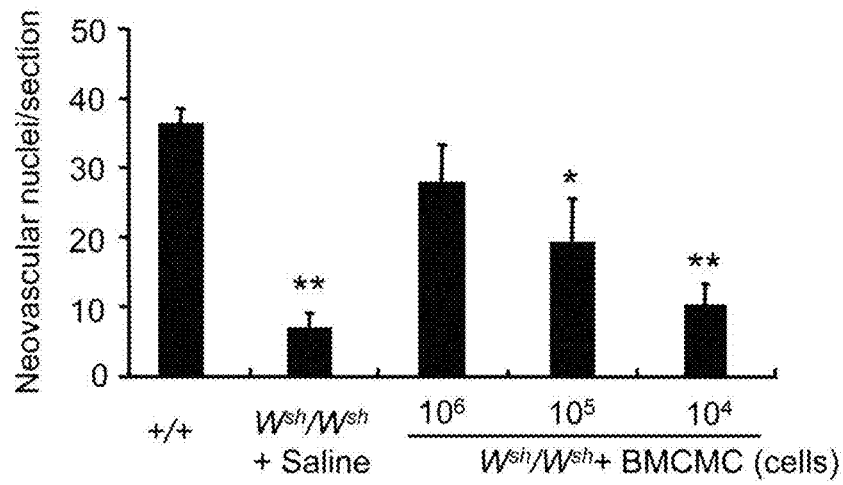
FIG. 4 is a graph which illustrates evaluation results of neovascularization of the mice in Reference Example 3. The abnormal revascularization region was increased by the preprocess with mast cells in various numbers. The data show the representative of two-individual tests using 3 ocular sections for respective groups. The number of neovascular nuclei in the ocular sections prepared from the P17 mice was counted after HE staining. The BMCMC dose-dependently enhanced the retinal neovascularization in the $W^{sh}/W^{sh}$ mice. The sign "*" denotes P<0.05, the sign "**" denotes P<0.01 (compared with the number of nuclei in the $+/+$ mice). Mean: ±SEM.

In the similar manners as Reference Example 2 except that the number of cells in the cell suspension of BMCMC was further controlled to $1 \times 10^5$ cells/20 μL or $1 \times 10^4$ cells/20 μL, respectively, BMCMC was injected to the mice by intraperitoneally, and evaluation of retinal neovascularization was carried out by using HE staining on neovascular nuclei of ocular sections on P17. The results are illustrated in FIG. 4. Note that in FIG. 4, the sign "*" denotes P<0.05 and the sign "**" denotes P<0.01 (compared with the number of nuclei of the eyes of the +/+ mice). The statistical significance was determined by one-way analysis of variance and Fisher's exact test. Error bars denote SEM.

As illustrated in FIG. 4, it was clarified that mast cells dose-dependently promotes retinal neovascularization in the eyes of the ROP models.

The results of the above-described Reference Examples 1-3 suggests that the presence of mast cells, or secretory components and granular components derived from the mast cells, promote abnormal neovascularization in the retinas of the ROP model mice.

Example 1

Influences of cromolyn, a mast cell stabilizer, on retinal neovascularization were examined as follows.

To examine an influence in various states of different oxygen concentration, mice for use in the tests were raised in a period from P0 to P17 according to the schedule in which the normal oxygen environment was used in the period P0-P7 (21 v/v % oxygen), the high oxygen concentration environment in the period P7-P12 (75 v/v % oxygen), and the normal oxygen environment in the period P12-P17. On P7 and P12, the oxygen concentration environment was replaced.

Figure 5:
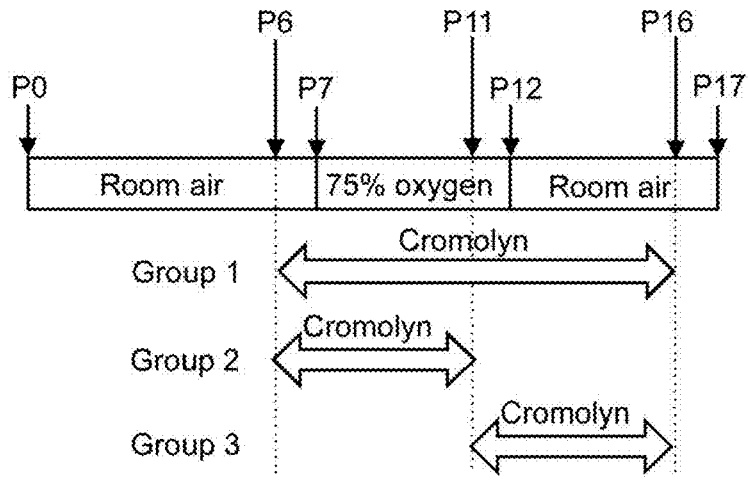
FIG. 5 is a drawing which illustrates an administration schedule for cromolyn in Example 1. Using the +/+ and $W^{sh}/W^{sh}$ mice, 20 µl, 50 mg/kg cromolyn or the vehicle was administered to neonatal mice by intraperitoneal injection for the period of P6-P16 for the first group, for the period of P6-P11 for the second group, and for the period of P11-P16 for the third group every day.

The neonatal mice of +/+ mice and the $W^{sh}/W^{sh}$ mice were divided into three groups, and cromolyn (a product of Sigma Aldrich Corporation) dissolved in phosphate buffered saline (PBS) was injected to the mice at the concentration of 50 mg/kg/20 µL intraperitoneally every day. PBS was administered to the control group at the same volume. Administration methods of the agent for the respective groups were as illustrated in FIG. 5.

Specifically, for the first group, cromolyn was administered to the neonatal mice from P6 to P16. For the second group, cromolyn was injected to the neonatal mice from P6 to P11. To the neonatal mice in the third group, cromolyn was administered from P11 to P16.

All animals were slaughtered on P17, and eyes were collected. Subsequently, similarly to Reference Example 1, the number of nuclei of the endothelial cell was counted after staining the ocular sections by HE, and thereby influences of cromolyn on the retinal neovascularization in the +/+ and $W^{sh}/W^{sh}$ neonatal mice was evaluated in the similar manner as Reference Example 1.

Figure 6A:
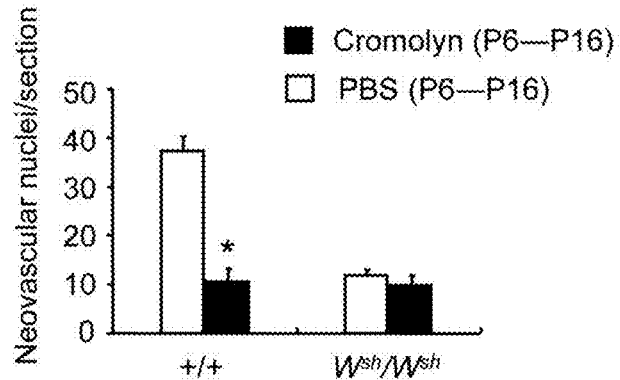
FIG. 6A is a graph which illustrates results of administration of cromolyn to the first group in Example 1. The process by cromolyn in the period of P6-P16 decreased pathological neovascularization in the +/+ mouse.
Figure 6B:
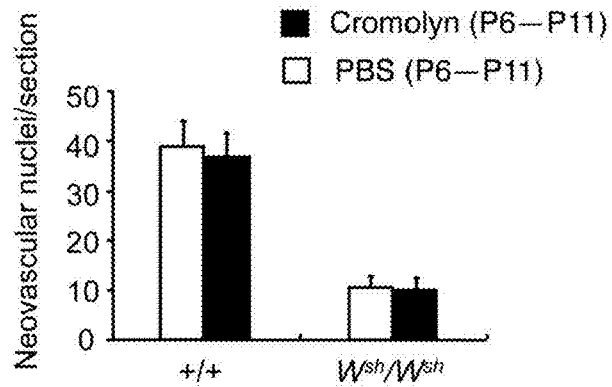
FIG. 6B is a graph which illustrates results of administration of cromolyn to the second group in Example 1. Cromolyn did not influence the abnormal growth of retinal blood vessels in the mice in the second group.
Figure 6C:
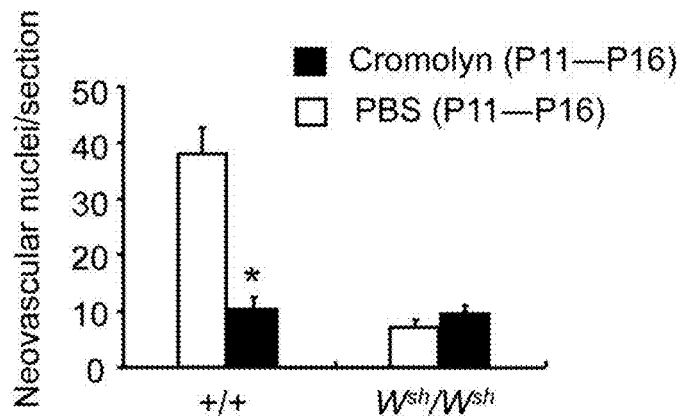
FIG. 6C is a graph which illustrates results of administration of cromolyn to the third group in Example 1. The neovascular chambers in the +/+ mice treated by cromolyn in the period of P11-P16 was less than those in the $W^{sh}/W^{sh}$ mice. The data show the representative of two-individual tests using 3 ocular sections for respective groups. The sign "*" denotes $P<0.01$ (compared with the number of nuclei in the control mice). Mean: ±SEM.

The results are illustrated in FIGS. 6A to 6C. Note that in FIGS. 6A to 6C, the sign "*" denotes P<0.01 (compared with the number of nuclei in the control mice).

As shown in FIGS. 6A to 6C, both the treatment with cromolyn in the period P6-P16 and the treatment with cromolyn in the period P11-P16 caused the neovascularization in the +/+ mice to a level as low as that in the $W^{sh}/W^{sh}$ mice. On the contrary, in the second group mice to which cromolyn was administered in the period P6-P11, cromolyn did not influence the growth abnormal vascular formation in the retinas.

In addition, in the case where degranulation of mast cells was inhibited by administration of cromolyn for 5 days (P11-P16) after exposure to the high oxygen concentration environment in the ROP models, it was shown, although no effect of inhibition by cromolyn was observed during the period of the high oxygen concentration environment (P6-P11), that the number of nuclei in the endothelial cell extending into the space of the vitreous body became significantly small (FIGS. 6B and 6C).

This suggests that neovascular components derived from mast cells possibly promoted retinal neovascularization due to the drastic change of the oxygen concentration after the exposure to the high oxygen concentration environment.

In addition, it is known that the administration of cromolyn has an effect of inhibiting neovascularization that may occur after having been exposed to the high oxygen concentration environment Example 2

Influences of nafamostat mesilate (NM) that is a specific inhibitor of tryptase on the ROP models were examined as follows.

For the ROP models, the BMCMC-injected $W^{sh}/W^{sh}$ mice produced in Reference Example 2 (administered by an amount of 1×10⁶ cells/20 µL) were used, and $W^{sh}/W^{sh}$ mice to which saline was administered by the same volume were used as the control group.

Figure 7:
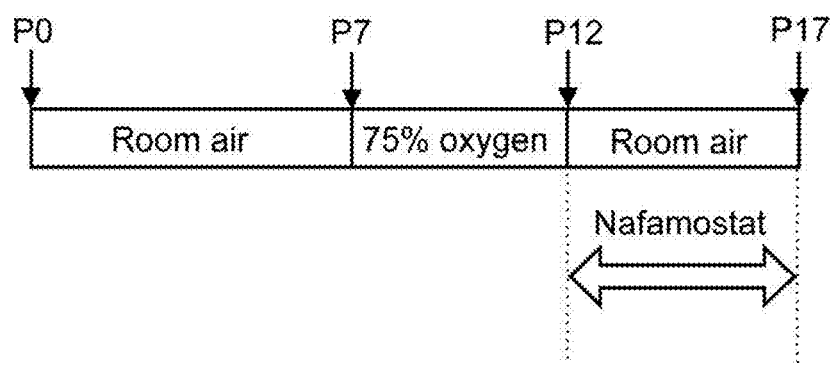
FIG. 7 is a drawing which illustrates an administration schedule for nafamostat mesilate in Example 2. 20 µl, 1 mg/kg NM or saline was injected to the neonatal mice by intraperitoneal injection every day. NM was injected to the mice in the period from P12 to P17.

The oxygen concentration for the period P0-P17 was replaced by the same schedule as Example 1 (see FIG. 7).

Figure 8:
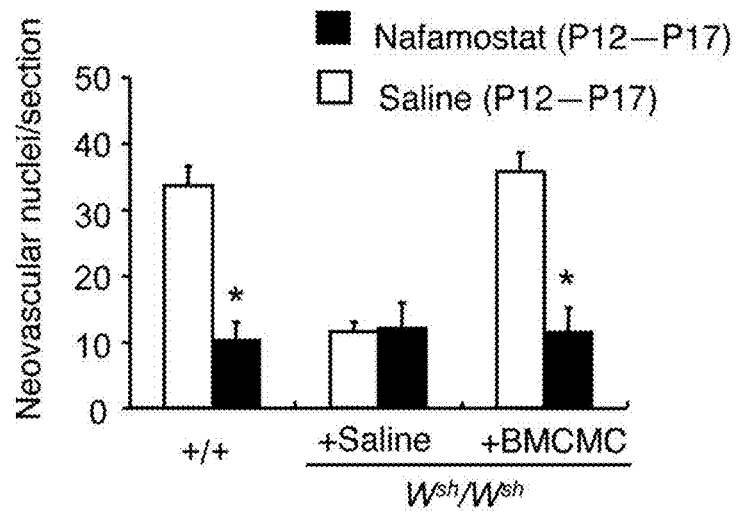
FIG. 8 is a graph which illustrates results of administration of nafamostat mesilate in Example 2. NM inhibited retinal neovascularization in the +/+ mice and the BMCMC-injected $W^{sh}/W^{sh}$ neonatal mice subjected to the ROP induction process. The data show the representative of four-individual tests using 3 to 4 ocular sections for respective groups. The sign "*" denotes $P<0.05$ (compared with the number of nuclei in the control mice). Mean: ±SEM.

1 mg/kg/20 µl NM dissolved in saline or saline was injected to the mice intraperitoneally in the period P12-P17 every day. On P17, the mice were slaughtered and eyes are collected, and evaluation of neovascularization was performed in the similar manner as Example 1. The results are illustrated in FIG. 8. In FIG. 8 the sign "*" denotes P<0.05 (compared with the number of nuclei of the endothelial cells of the vessels of the control mice).

As shown in FIG. 8, NM inhibited retinal neovascularization in the +/+ mice and the BMCMC-injected $W^{sh}/W^{sh}$ mice to which ROP was induced. This shows that by administering NM, the neovascular nuclei in the vitreous body of the +/+ mice and the BMCMC-injected $W^{sh}/W^{sh}$ mice with ROP could be decreased on P17.

It is therefore found that both tryptase inhibitors and mast cell stabilizers can be used for prophylaxis or therapy of ROP.

Example 3

It was examined that tryptase is available for use as a marker for ROP in the following manner.

The BMCMC-injected $W^{sh}/W^{sh}$ mice prepared in Reference Example 2 (administered by a volume of 1 multiply 10⁶ cells/20 µL) were used as a mast cell-present group while $W^{sh}/W^{sh}$ mice to which saline was administered by the same volume were used as a mast cell-absent group. In addition, the +/+ mice were used as a control group. To the groups, an exemplary number of 4 to 5 mice was assigned per one group.

For all animals of each group, the oxygen concentration environment in the period P0-P7 was varied by the same schedule as that in Example 1.

On P17, blood was collected from the respective mice to obtain serum by a conventional method. This serum was diluted by 10-fold dilution for quantification of tryptase. For the quantification of tryptase in serum, a commercial ELISA kit (TPS-conjugated immunoadsorption measurement kit (mouse), USCN Life Science Inc., Cat. No. E91070 Mu) was used, and the kit was operated conforming to the instruction manual of the kit. The color reaction time was appropriately controlled so as to prevent the reactions from progressing too rapidly to perform the measurement. For measurement of absorbance, a microtiter plate reader (ImmunoMini NJ-2300, a product of NalgeNunc) was used. The statistical significance was determined by one-way analysis of variance and Fisher's exact test. Error bars denote SEM. The sign "**" denotes P<0.01 (compared with the concentration of serum tryptase for the saline-dosed mice).

Figure 9:
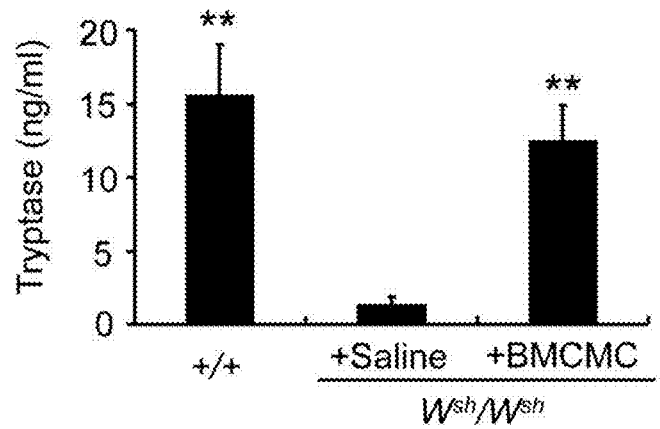
FIG. 9 is a graph which illustrates results of measurement of serum tryptase in Example 3. Compared with the saline-dosed $W^{sh}/W^{sh}$ neonatal mice, the value of the serum tryptase concentration was high in the +/+ and the BMCMC-injected $W^{sh}/W^{sh}$ neonatal mice. The number n=5, the sign "**" denotes $P<0.01$ (compared with the serum tryptase level of the saline-dosed $W^{sh}/W^{sh}$ neonatal mice).

As shown in FIG. 9, when ROP was induced in the +/+ mice in which mast cells were present and the BMCMC-dosed $W^{sh}/W^{sh}$ mice on P17, the value of concentration of serum tryptase was high for each such group. On the other hand, the value of the concentration of serum tryptase was extremely low for the $W^{sh}/W^{sh}$ mice in which no mast cell was present.

As described in Reference Example 2, in both groups of the +/+ mice and the BMCMC-dosed $W^{sh}/W^{sh}$ mice, retinal neovascularization occurred on P17 due to the change of the oxygen concentration and thus ROP was induced, while in the $W^{sh}/W^{sh}$ mice in which no mast cell was present, no retinal neovascularization occurred and ROP was not induced. The results of this Example show that the concentration of serum tryptase was high for the group to which ROP was induced. This shows that tryptase in blood is useful as an index for determination of ROP.

Example 4

Influences of neutralization of tryptase on retinal neovascularization in the ROP model were evaluated in the following manner.
<Materials>
1. Reagent
(1) Mouse mast cell-protease-6/Mcpt6 antibody.
Monoclonal rat $IgG_{2A}$ (R & D Systems, #MAB4288, 500 µg)
(2) Control
Rat $IgG_{2A}$ isotype control (R & D Systems, #MAB006, 500 µg)
2. Mouse
C57BL/6-+/+(+/+) and C57BL/6-$W^{sh}/W^{sh}$($W^{sh}/W^{sh}$) neonatal mice
3. Cell
Bone marrow-derived cultured mast cells (BMCMC)
<Method>
1. On P1 or P2, BMCMC ($1\times10^6$) 20 µl included in saline was injected to the $W^{sh}/W^{sh}$ neonatal mice intraperitoneally.
2. Between P7 and P12, the neonatal mice were exposed to the high oxygen concentration environment.
3. On P12, the oxygen concentration environment was returned to the normal oxygen environment (room air).
4. Between P12 and P17, a 0.2 µg/20 µl Mcpt6 antibody or isotype control was injected once a day.
5. On P17, eyes are collected and then fixed with Davidson's fixative.
6. The samples were stained by HE, and the number of nuclei of the endothelial cell was counted as the number of neovascular cells.
<Result>
The measurement results are illustrated in FIG. 10 and Table 1.

TABLE 1

| Mouse | Injection | Neovascular nuclei/section (Mean ± SEM) |
|---|---|---|
| +/+ | Isotype control (n = 9) | 32.5 ± 3.3 |
|  | Mcpt6 antibody (n = 6) | 1.4 ± 0.5 |
| $W^{sh}/W^{sh}$ + BMCMC | Isotype control (n = 9) | 35.0 ± 9.5 |
|  | Mcpt6 antibody (n = 6) | 5.0 ± 2.7 |

Figure 10:
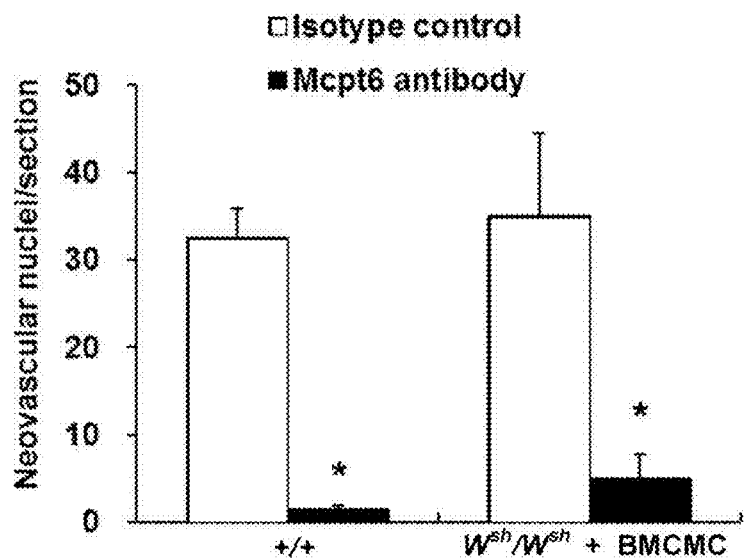
FIG. 10 is a graph which illustrates results of administration of the anti-tryptase neutralizing antibody in Example 4. The anti-tryptase neutralizing antibody inhibited the retinal neovascularization in the +/+ and BMCMC-injected $W^{sh}/W^{sh}$ neonatal mice subjected to the ROP induction process. The sign "*" denotes $P<0.01$ (compared with the number of nuclei in the control mouse).

As can be understood from FIG. 10 and Table 1, in the ROP-induced +/+ mice and the BMCMC-injected $W^{sh}/W^{sh}$ mice, the anti-tryptase neutralizing antibody inhibited retinal neovascularization. This shows that by administering the anti-tryptase neutralizing antibody, the neovascular nuclei in the vitreous body of the +/+ mice and the BMCMC-injected $W^{sh}/W^{sh}$ mice to which ROP was induced could be decreased on P17.

Therefore, it is understood that the anti-tryptase neutralizing antibody as an tryptase inhibitor is available for prophylaxis or therapy of ROP.

Example 5

Influences of cromolyn, which has been verified in Example 1 as being capable of inhibiting retinal neovascularization induced due to the change of the oxygen concentration, and of seven compounds that are the candidate substances, on degranulation of mast cells were examined by the following method by using β-hexosaminidase as the marker substance.
(1) Preparation of Mast Cell Suspension
It has been known that human mast cell strain HMC-1 is a cell strain derived from leukemia, that it has a characteristic as a mast cell, and that it includes β-hexosaminidase in its granules. With reference to a previous report (European Journal of Immunology, Vol. 29, 2645-2649 (1999)), HMC-1 cells were suspended in an α-MEM culture medium to which 10% (v/v) fetal calf serum and a usual dose of antibiotic had been added for preparation of a mast cell suspension with a cell concentration of $5\times10^5$ cells/ml. Throughout the test period including the period in the high oxygen concentration environment, all the cells were subjected to an environment of 5% (v/v) $CO_2$, 37° C. as the cultivation condition other than the oxygen concentration.
(2) Addition of Cromolyn and the Candidate Substance
The mast cell suspension was dispensed on a 96-well plate at $4\times10^5$ cells/well. Cromolyn and each of the seven candidate substances were added to obtain the following concentrations. As controls (media) to which the agent was not added and as non-treated examples to which the marker substance release induction process was not carried out, wells to which neither cromolyn nor the candidate substances was added were set.

Cromoglycic acid (Cromolyn), 10 ng/ml (J Immunol. 2010. 185(1): 709-716)

Suplatast, 10 µM (J Immunol. 2009. 183(3): 2133-41; Transpl Immunol. 2007. 18(2): 108-14)

Tranilast, 10 µM (Tohoku J Exp Med. 2009. 217(3): 193-201; Circ Res. 2008. 102(11): 1368-77; Jpn J Pharmacol. 1988. 46(1): 43-)

Amelexanox, 1 µM (2012. Orphanet J Rare Dis. 7:58; J Biol Chem. 2000. 275(42): 32753-62; Arerugi. 1990. 39(10): 1448-54; Int Arch Allergy Appl Immunol. 1987. 82(1): 66-71)

Levocabastine, 10 nM (Exp Eye Res. 1996. 63(2): 169-78)

Ibudilast, 1 µM (J Biol Chem. 2012. 287(45): 37907-16; PLoS One. 2011. 6(4):e18633; Eur J Pharmacol. 2011. 650 (2-3): 605-11.; J Biol Chem. 2012. 287(45):37907-16; PLoS One. 2011. 6(4):e18633; Eur J Pharmacol. 2011. 650 (2-3): 605-11)

Epinastine, 1 ng/ml (Clin Exp Allergy. 2007. 37(11): 1648-56)

Pemirolast, 10 nM (J Pharmacol Exp Ther. 2011. 337(1): 226-35; Cell Mol Neurobiol. 2006. 26(3): 237-46)

Note that the literatures recited after the substances were literatures referred to in setting the dose of the substances.
(3) Marker Substance Release Induction Process and Step for Contact with Cromolyn or Candidate Substance The marker substance (β-hexosaminidase) release induction process and the step for contact with the mast cells HMC-1 that had been subjected to the marker substance release induction process were performed by retaining the 96-well plate in the high oxygen concentration environment (75 v/v % oxygen) for 24 hours and in the normal oxygen environment (20 v/v % oxygen) for 12 hours. For the non-treated example, the 96-well plate was retained in the normal oxygen environment (20 v/v % oxygen) for 24 hours and further retained in the normal oxygen environment for 12 hours.

(4) Marker Substance Detection Step

The detection and measurement of the marker substance (β-hexosaminidase) that had been released by degranulation of the mast cells in the contacting step were carried out by a previously reported method (Eur. J. Immunol. 19 (1989) 2251-2256). To put it briefly, the step was carried out in the following manner. After having collecting the supernatant from the respective wells after the contacting step, the pellets (cells) were dissolved in a 0.5% triton X-100-containing α-minimal essential medium (α-MEM: a product of Gibco) at the same volume. In the respective wells of the 96-well plate, 5 μl supernatant or cell lysates were mixed with a 50 μl substrate solution (1.3 mg/ml p-nitrophenyl-N-acetyl-β-D-glucosamine;

pH 4.5 in 100 mM sodium citrate). After incubation at 37° C. for 60 minutes, 150 μl, 200 mM solution of glycine (pH 10.7) was added, and the reaction was stopped. The absorbance was measured at 414 nm. The (%) of the released marker substance (β-hexosaminidase) was calculated according to the following expression;

OD(supernatant)/(OD(supernatant).+OD(pellet))×100.

The ratio (%) of the released marker substance (β-hexosaminidase) denotes the degree of degranulation, and if this ratio is decreased, the decrease indicates that the degranulation has been inhibited.

The test was performed by three-sample test, an average and standard deviation were calculated on the basis of the measurement results for statistic analysis by ANOVA+Tukey's test.

(5) Results

Figure 11:
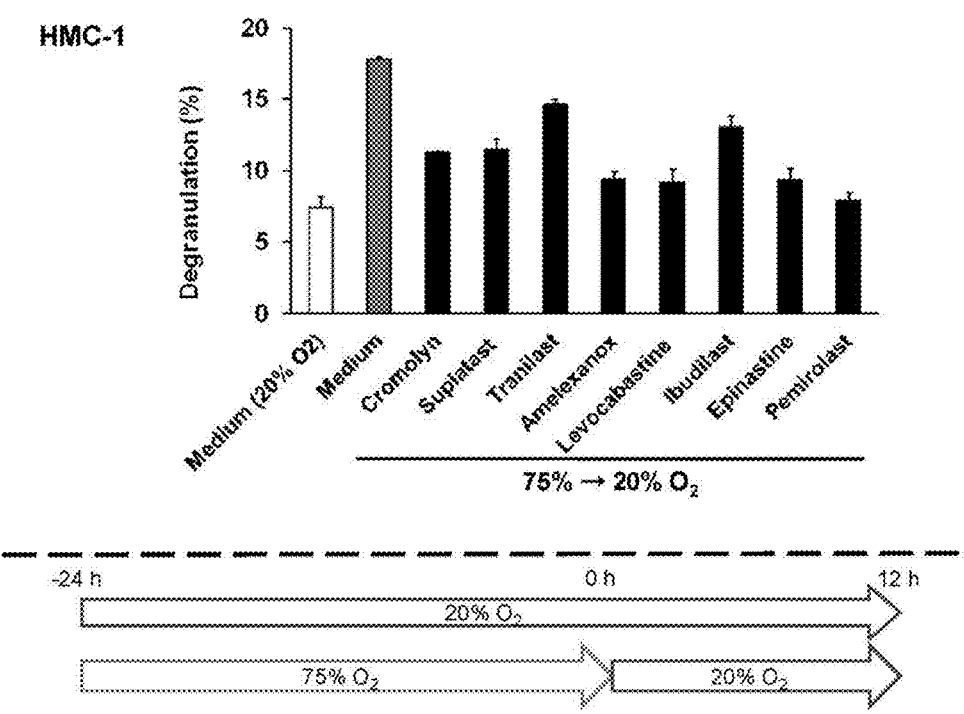
FIG. 11 is a drawing which illustrates inhibition by seven candidate substances in Example 5 of degranulation of mast cells induced by variation of the oxygen concentration similarly to cromolyn that has been verified by Example 1 to inhibit retinal neovascularization.

The measurement results are illustrated in FIG. 11. Referring to FIG. 11, in the controls (media) that had undergone the marker substance release induction process, degranulation was more promoted compared with the non-treated examples (media (20% $O_2$)) that were not subjected to the marker substance release induction process. Specifically, it was shown that also in an in vitro test system using HMC-cells, as with in vivo ROP model (Example 3), release of granular contents of mast cells would occur due to decrease of the oxygen concentration caused by shifting from the high oxygen concentration environment to the normal oxygen environment. In this test system, similarly to cromolyn, all the seven candidate substances (suplatast, tranilast, amlexanox, levocabastine, ibudilast, epinastine, and pemirolast) inhibited the degranulation induced by variation of the oxygen concentration more excellently compared with the controls (media), and the inhibition effect of all these substances was statistically significant ($p<0.05$). It has been known that cromolyn is a mast cell stabilizer, and it has been verified by Example 1 that it inhibits retinal neovascularization induced by variation of the oxygen concentration. Accordingly it is considered that the seven candidate substance, similar to cromolyn tested in Example 1, have an effect of inhibiting retinal neovascularization and are capable of curing and preventing ROP.

INDUSTRIAL APPLICABILITY

The present invention is capable of providing the therapeutic or prophylactic agent for ROP, the testing method for ROP, and the method for screening the therapeutic or prophylactic substance that are suited to the pathogenic mechanism of ROP and highly effective, and thus the present invention is industrially useful.

The invention claimed is:

1. A method for testing and treating retinopathy of prematurity comprising:
   detecting a marker substance that is released by degranulation of mast cells from a biological sample derived from a subject;
   determining that the subject has been affected by retinopathy of prematurity or that the subject needs therapy or prophylaxis of retinopathy of prematurity based on a detected amount of the marker substance; and
   intravenously administering a therapeutic or prophylactic agent for retinopathy of prematurity comprising at least one compound selected from the group consisting of tryptase inhibitors and mast cell stabilizers as an active ingredient to a subject needing therapy or prophylaxis of retinopathy of prematurity by an amount effective for the therapy or prophylaxis therefor for 5 to 10 days starting from earlier than or at the timing of shift of oxygen concentration around the subject, and
   wherein the marker substance is β-hexosaminidase, and
   wherein the biological sample is derived from at least one selected from the group consisting of a tissue, a body fluid sample, a urine sample, a lacrimal fluid and a sample from a leukocyte fraction and an erythrocyte fraction in blood of a subject.

2. The method for testing and treating retinopathy according to claim 1, wherein the tryptase inhibitors are administered in an amount of 0.01 mg/day to 500 mg/day per postnatal weight (kg) of the individual.

3. The method for testing and treating retinopathy according to claim 1, wherein the mast cell stabilizers are administered in an amount of 0.0001 mg/day to 500 mg/day per postnatal weight (kg) of the individual.

4. The method for testing and treating retinopathy according to claim 1, wherein the biological sample is a tissue that is a vitreous body or a body surface tissue.

5. The method for testing and treating retinopathy according to claim 1, wherein the biological sample is a body fluid sample that is blood, plasma, serum, lymph or aqueous humor.

6. The method for testing and treating retinopathy according to claim 1, wherein the therapeutic or prophylactic agent is at least one selected from the group consisting of Nafamostat, an anti-tryptase antibody and cromolyn.

7. The method for testing and treating retinopathy according to claim 1, wherein the therapeutic or prophylactic agent is at least one selected from the group consisting of pemirolast, amlexanox, tranilast, ibudilast, suplatast, levocabastine and epinastine.

* * * * *